(12) United States Patent
Vold et al.

(10) Patent No.: US 9,482,644 B2
(45) Date of Patent: Nov. 1, 2016

(54) METHODS AND APPARATUS FOR HIGH-RESOLUTION CONTINUOUS SCAN IMAGING USING VOLD-KALMAN FILTERING

(71) Applicant: ATA Engineering, Inc., San Diego, CA (US)

(72) Inventors: Havard I. Vold, Charleston, SC (US); Parthiv N. Shah, San Diego, CA (US)

(73) Assignee: ATA ENGINEERING, INC., San Diego, CA (US)

( * ) Notice: Subject to any disclaimer, the term of this patent is extended or adjusted under 35 U.S.C. 154(b) by 225 days.

(21) Appl. No.: 14/470,797

(22) Filed: Aug. 27, 2014

(65) Prior Publication Data

US 2015/0090036 A1 Apr. 2, 2015

Related U.S. Application Data

(60) Provisional application No. 61/879,061, filed on Sep. 17, 2013.

(51) Int. Cl.
| | |
|---|---|
| *G01N 29/00* | (2006.01) |
| *G01N 29/06* | (2006.01) |
| *G03H 3/00* | (2006.01) |
| *G03H 1/04* | (2006.01) |

(52) U.S. Cl.
CPC ........ *G01N 29/0663* (2013.01); *G03H 1/0443* (2013.01); *G03H 3/00* (2013.01)

(58) Field of Classification Search
CPC .......... G03H 3/00; G03H 3/125; G03H 1/08; G03H 1/0866; G03H 2227/03; G01N 29/0663
USPC ................................... 73/603, 643; 702/109
See application file for complete search history.

(56) References Cited

U.S. PATENT DOCUMENTS

| 4,483,195 A * | 11/1984 | Brown | G01L 11/00 73/112.01 |
|---|---|---|---|
| 5,010,576 A * | 4/1991 | Hill | G10K 11/1784 381/71.14 |
| 5,526,292 A * | 6/1996 | Hodgson | G10K 11/1788 244/1 N |
| 5,618,010 A * | 4/1997 | Pla | G10K 11/1788 181/206 |
| 5,754,662 A * | 5/1998 | Jolly | G10K 11/1786 381/71.11 |
| 5,986,971 A * | 11/1999 | Kim | G03H 3/00 367/8 |
| 6,004,095 A * | 12/1999 | Waitz | B64C 21/025 415/115 |
| 8,843,342 B2 * | 9/2014 | Vold | G03H 3/00 702/109 |
| 2004/0114768 A1 * | 6/2004 | Luo | G10K 11/1788 381/71.4 |

(Continued)

*Primary Examiner* — Helen Kwok
(74) *Attorney, Agent, or Firm* — Lorenz & Kopf, LLP

(57) ABSTRACT

A method of imaging a test subject includes providing one or more moveable sensors to sense an attribute of the test subject (e.g., acoustic pressure), wherein the attribute has a tonal noise component and a broadband noise component. A rotational sensor is provided to sense a rotational velocity of a rotational element of the test subject. Each of the moveable sensors are moved along a path while continuously acquiring test data that is indicative of the rotational velocity of the rotational element, the sensed attribute, the position, and the orientation of each of the moveable sensors. A set of transfer functions corresponding to points in space that have been visited by the moveable sensors are constructed, each of the transfer functions relating the test data of the moveable sensors to the test data of the rotational sensor. A visual representation of the tonal noise component of the attribute in a region adjacent the test subject is produced using the set of transfer functions.

20 Claims, 34 Drawing Sheets
(18 of 34 Drawing Sheet(s) Filed in Color)

(56) References Cited

U.S. PATENT DOCUMENTS

2011/0120222 A1* 5/2011 Scholte .................. G01H 3/125
73/603

2015/0043744 A1* 2/2015 Lagodzinski .......... H04R 3/002
381/73.1

* cited by examiner

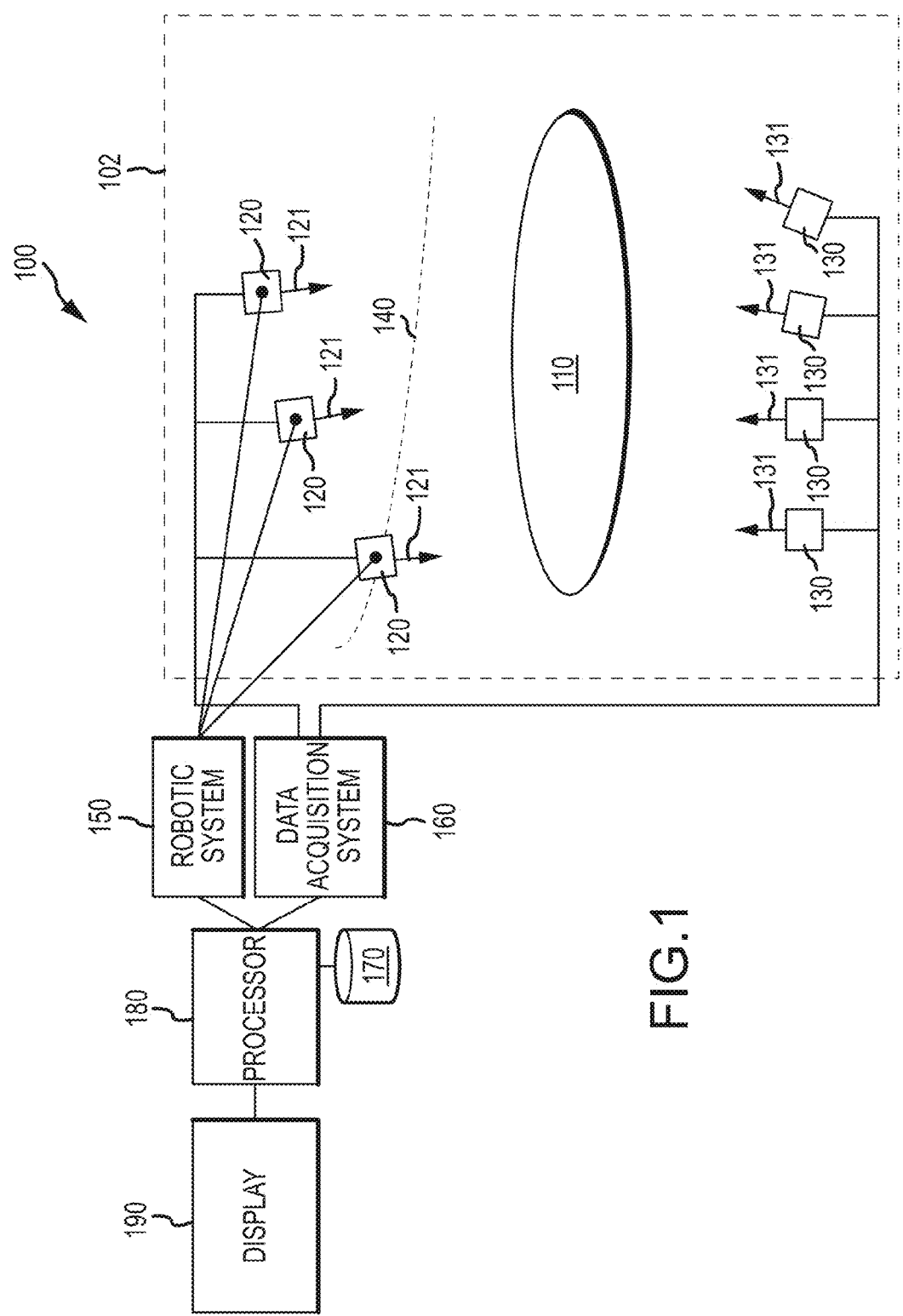

METHODS AND APPARATUS FOR HIGH-RESOLUTION CONTINUOUS SCAN IMAGING USING VOLD-KALMAN FILTERING

CROSS-REFERENCE TO RELATED APPLICATIONS

This application claims priority to U.S. Prov. Pat. App. Ser. No. 61/879,061, filed Sep. 17, 2013, the entire contents of which are hereby incorporated by reference.

TECHNICAL FIELD

Embodiments of the subject matter described herein relate generally to imaging techniques and, more particularly, to three-dimensional imaging of test subjects.

BACKGROUND

It is often desirable to scan a test subject and/or a three-dimensional area around a test subject using some form of imaging technique. Acoustical holography, for example, is a method often used to characterize the surface velocities and acoustic pressures of coherently vibrating structures such as engines and gearboxes.

For aeroacoustic noise sources such as jets with multiple partially-correlated source mechanisms, scan-based techniques using reference and response transducers and singular value decomposition have been applied to acoustical holography to decompose a noise source into partial fields. The partial fields can reconstruct an overall sound field and also provide a near-field representation of the source that can help in understanding the physics of jet noise.

The acoustic source characteristics of jet plumes from high performance commercial turbofan engines are not well defined, however. This is due to the difficulty in making a complete set of descriptive acoustic measurements characterizing the size, intensity, directivity, and distribution of the acoustic source (i.e., jet plume).

Acoustic near-field acoustic holography concepts have been proposed for full-scale jet engines. An acoustic hologram is a phase-locked "picture" of a spatially coherent pressure (or velocity) field that corresponds to an equivalently vibrating surface at the measured points. Acoustic holograms are typically presented on a frequency by frequency basis. By making successive array measurements ("scans") over a sufficiently large hologram surface in a source-free region, this technique allows, in theory, for an inverse propagation of the wavenumber spectrum of the measured surface pressures to any surface closer to (but still containing) the source, as well as a complete description of the sound field further away from the source. Aeroacoustic sources such as jets do not actually produce a spatially coherent pressure field, so an acoustical holography system for high-speed jets must approximate the sound source as a number of mutually incoherent acoustic holograms ("partial fields").

Furthermore, some test subjects may include one or more rotating shafts, which may be coupled mechanically through various gears, belts, chains, and the like, and/or might be electronically coupled via a feedback system. The rotations of these shafts will cause periodic "tonal" or "deterministic" noise, modulated by the various mechanical components of the test subject itself. Characterization and separation of the deterministic components from the random or "non-deterministic" components using prior art techniques can be computationally complex and/or inaccurate.

It is therefore desirable to provide imaging systems and methods that are efficient, fast, and allow three-dimensional scanning to be performed using a reduced number of sensors, particularly in cases where the test subject includes one or more rotating components. Other desirable features and characteristics of the present invention will become apparent from the subsequent detailed description and the appended claims, taken in conjunction with the accompanying drawings and the foregoing technical field and background.

BRIEF DESCRIPTION OF THE DRAWINGS

The patent or application file contains at least one drawing executed in color. Copies of this patent or patent application publication with color drawing(s) will be provided by the Office upon request and payment of the necessary fee. A more complete understanding of the subject matter may be derived by referring to the detailed description and claims when considered in conjunction with the following figures, wherein like reference numbers refer to similar elements throughout the figures.

FIG. 1 is a conceptual block diagram of an imaging system in accordance with one embodiment of the invention;

DETAILED DESCRIPTION

Figure 3:
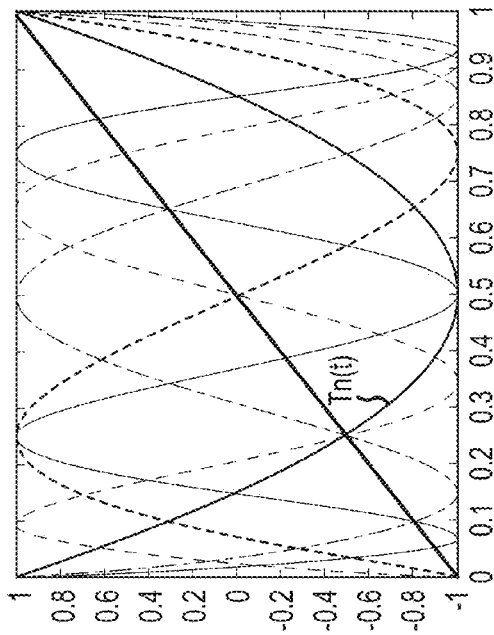
FIG. 3 is a graph depicting a set of Chebyshev polynomials associated with the graph of FIG. 1.

The following detailed description is merely illustrative in nature and is not intended to limit the invention or the application and uses of the invention. Furthermore, there is no intention to be bound by any expressed or implied theory presented in the preceding technical field, background, brief summary or the following detailed description. For the purposes of conciseness, many conventional techniques and principles related to imaging, acoustics, data acquisition, jet exhaust, and the like are not described in detail herein.

Techniques and technologies may be described herein in terms of functional and/or logical block components and various processing steps. It should be appreciated that such block components may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

In general, the present invention relates to a continuous scanning method employing one or more moveable sensors and one or more reference sensors deployed in the environment around a test subject. Each sensor is configured to sense an attribute of the test subject (e.g., sound energy, infrared, etc.) while continuously moving along a path and recording the sensed attribute, the position, and the orientation of each of the moveable sensors and each of the reference sensors. The system then constructs a set of transfer functions corresponding to points in space visited by the moveable sensors, wherein each of the transfer functions relate the test data of the moveable sensors to the test data of the reference sensors. In this way, a graphical representation of the attribute in the vicinity of test subject can be produced.

In one embodiment, in which the test subject includes one or more rotating elements, a tachometer or other rotational sensor is coupled to the rotational elements to provide a synchronous time history of the rotating element's position, providing phasing information that allows tonal components to be separated from random components. In one embodiment, Vold-Kalman order extraction is employed to accomplish this separation.

In one embodiment, finite-element-type basis functions (such as Chebyshev polynomials) are used to produce a full two-dimensional (2D) surface scan using a set of one-dimensional (1D) linear scans. In a further embodiment, canonical coherence-based partial field estimation is used to accurately compute transfer functions to describe the source using fewer partial fields (i.e., principal components).

Referring now to FIG. 1, an imaging system in accordance with one embodiment generally includes a test environment 102 (e.g., a room, chamber, or simply an abstract spatial region) in which a test subject 110 has been placed. Test subject 110 may be any type of object (which may be organic, nonorganic, a life form, etc.) or phenomena having an attribute (sound energy, heat energy, an internal component or structure, etc.) to be sensed. In one embodiment, as described in detail below, test subject 110 is a high speed jet or jet engine, and the sensed attribute is sound energy (or "noise") produced by the jet engine during operation. In this regard, while the invention is often described in the context of imaging an acoustic hologram (or partial fields) around an operating jet exhaust, this example is used without loss of generality. The continuous scanning methods described herein may be used to sense a wide variety of attributes of many types of objects or phenomena.

One or more moveable sensors 120 are provided within environment 102. Each sensor 120 is coupled to a robotic system 150 and a data acquisition system 160. Similarly, one or more reference or "stationary" sensors 130 are also provided within environment 102, and are coupled to data acquisition system 160. Each moveable sensor 120 has a spatial position and an orientation 121. Each reference sensor 130 (which is generally stationary) also has a corresponding orientation 131. The various sensors may be of the same "type" (e.g., acoustic pressure sensors), or may simply be capable of producing respective signals such that the signals from the reference sensors are a function of the signals from the moveable sensors, and thereby relate directly or indirectly to the same attribute.

Robotic system 150 and data acquisition system 160 are communicatively coupled to a processor 180, which itself is communicatively coupled to a display 190 (e.g., an LCD or other such display) and a storage unit 170 (e.g., a solid-state drive, a hard drive, etc.). The various functional blocks 180, 150, 170, 190, and 160 may be implemented in any combination of hardware, firmware, and software. In one embodiment, for example, display 190, processor 180, and storage unit 170 are integrated into a general purpose computer with a suitable I/O interface (not shown) to robotic system 150 and data acquisition system 160. In a further embodiment, data acquisition system 160 is also integrated (via hardware and/or software) into processor 180.

Robotic system 150, under control of processor 180, is configured to cause each moveable sensor 120 to move along a path 140, which is typically predefined or otherwise known a priori by the system. The term "robotic system" is used in the general sense of any mechanical system that causes movement within a three-dimensional space through any convenient articulation scheme. Thus, this term comprehends the use of a wide variety of systems, ranging from simple rotating structures to complex, multi-axis robotic arms.

Data acquisition system 160 is configured to acquire scan test data associated with subject 110 while robotic system 150 moves sensors 120 along their respective paths 140, including corresponding position/orientation data of sensors 120. In preferred embodiments, the data acquisition system acquires the test data in a continuous manner as the sensors 120 are moved. The test data is then stored (e.g., within storage unit 170) and analyzed by processor 180 to produce a three-dimensional representation of the attribute, which may then be displayed on display 190. Data acquisition system 160 may include any number of software and hardware components capable of performing the desired acquisition of data, including conventional data acquisition systems known in the art.

The scanning by data acquisition system 160 is "continuous" in that, in contrast to "discrete" scanning, the moveable sensors 120 do not move to a discrete location, allow data acquisition system 160 to take one or more measurements, then move on to the next discrete location; rather, data acquisition system 160 acquires the test data substantially continuously as the moveable sensors 120 move along their paths 140. At the same time, data acquisition system 160 acquires data from reference sensors 130.

The position and orientation of each moveable sensor 120 (e.g., x, y, z Cartesian coordinates and an orientation vector) may be determined from robotic system 150, or may determined in real time via a locationing method. For example, each sensor 120 may include a GPS, RFID, WiFi, or other locationing component that sends positional and/or orientation data (e.g., wirelessly) to data acquisition system 160 and/or processor 180. Such a positioning scheme might be advantageous, for example, in a "hand held" wand or other such embodiment where an operator can move the sensors around a test subject in an arbitrary manner.

At the end of the scanning process (or during the scan), test data along paths 140 and at the reference sensors 120 will be available for analysis by processor 180. Processor 180 takes this data (which only represents data for a limited number of paths in environment 102 within a particular range of time) to construct a more complete set of data representing a full scan of test subject 110, as will be discussed in further detail below.

Moveable sensors 120 may be rigidly coupled to each other (e.g., along a linear array), or may be independently controlled. In a particular embodiment, for example, moveable sensors 120 are rigidly coupled and distributed along a linear structure configured to rotate around test subject 110.

Figure 5:
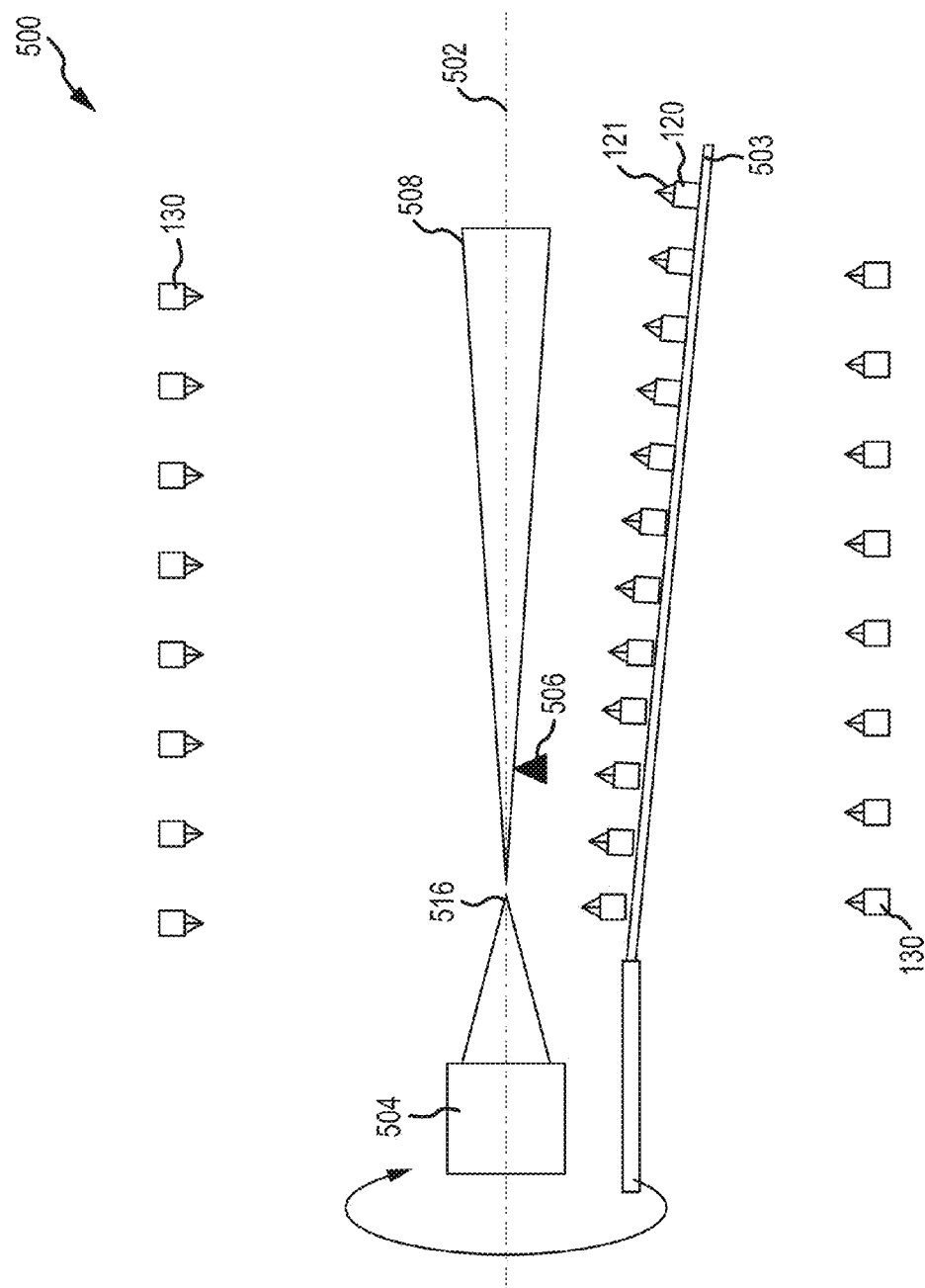
FIG. 5 is an overview of an imaging system in accordance with an exemplary embodiment of the invention.

More particularly, FIG. 5 depicts a scanning system 500 configured to sense sound energy produced by a jet exhaust 508 exiting the nozzle 516 of a plenum 504. FIG. 5 schematically depicts a top view of the test environment. As shown, plenum 504, nozzle 516, and jet exhaust 508 are generally coaxially oriented along an axis 502. A set of moveable sensors 120 (e.g., twelve sensors) are rigidly coupled to a structure or "boom" 503 and spaced equidistantly at intervals of approximately 10 cm.

Boom 503 (which comprises one component of robotic system 150 shown in FIG. 1) is configured to rotate around axis 502 while maintaining the orientation 121 of sensors 120 facing toward jet exhaust 508. That is, during a scanning process, boom 503 rotates partially or completely about axis 502, traversing a conical (or cylindrical) path that at least partially circumnavigates test subject 110. The resulting paths (140 in FIG. 1) described by respective moveable sensors 130 will thus consist of a series of circles, each lying within a plane orthogonal to axis 502.

While boom 503 is shown as being non-parallel to axis 502, embodiments of the invention are not so limited. Depending upon the application, and the nature of the test subject, it might be advantageous for boom 503 to be parallel to axis 502 and/or to change its orientation during a scan process. Also illustrated in FIG. 5 are a series of reference sensors 130. In one embodiment, two or more sets of linearly distributed reference sensors 130 (e.g., eight sensors per set) are employed, as shown, each having an orientation generally facing exhaust 508.

Figure 20:
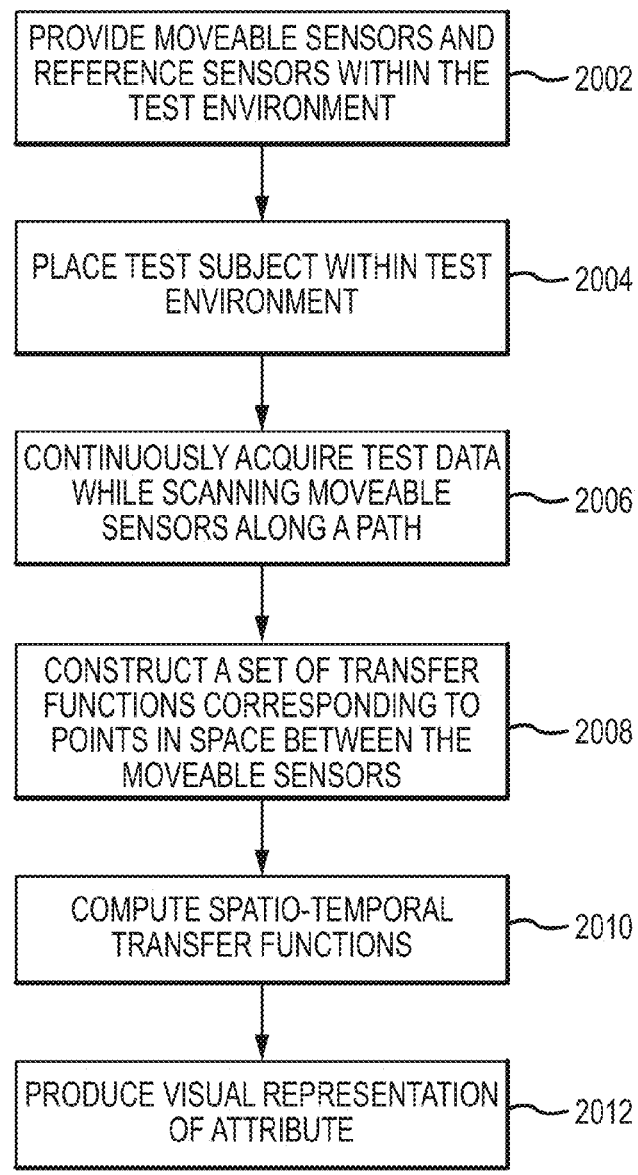
FIG. 20 is a flowchart depicting a method in accordance with one embodiment.

Referring now to FIG. 20 in combination with FIG. 1, an exemplary imaging method will now be described. In general, the experimental setup begins with the provision of various moveable sensors 120 and reference sensors 130 (Step 2002), and placement of the test subject 110 within the test environment 102. The position, orientation, and number of such sensors will vary depending upon the nature of the test subject and other factors. In many embodiments, it is desirable to utilize multiple sets of reference sensors on generally opposite sides of the test subject.

Next, in step 2006, the moveable sensors are translated and/or rotated with respect to test subject 110 using robotic system 150. At the same time, test data is continuously acquired by data acquisition system 160. This test data will include data relating to the attribute being sensed, as well as orientation and position data, as described above. The test data is then suitably stored, for example, in storage 170.

Next, in step 2008, the system (e.g., processor 180) analyzes the acquired test data and constructs transfer functions at points in space visited by moveable sensors 120 (the transfer functions relating the moveable sensors 120 to reference sensors 130). The nature of this calculation will be described in further detail below.

Next, in step 2010, processor 180 computes spatio-temporal transfer functions associated with the test data. In this way, a full set of transfer functions can be estimated between the relatively low number of reference sensors and moveable sensors at an arbitrary point in space around test subject 110. This calculation will also be described in further detail below.

Finally, in step 2012, a visual representation of the scanned attribute is produced (e.g., via display 190). This visual representation may take any desired form, including various 2D or 3D mappings. Example display types will be described below in connection with FIGS. 14 and 15.

Having thus described various sensor configurations and a general method in accordance with embodiments of the invention, an exemplary method for constructing the desired three-dimensional visualization will now be described in detail in the context of jet exhaust noise.

First, it is assumed in the following discussion that the sound source (e.g., exhaust 508, or a point source) is a statistically stationary random process. Due to the large volumetric extent of the acoustic source and a relatively small hologram array aperture, sensors 120 ("response microphones," or simply "microphones") are moved in successive scans to cover an entire hologram surface (i.e., an abstract surface encompassing exhaust 508). As the source is described by multiple mutually uncorrelated, spatially coherent sound fields, a set of N reference microphones is distributed in space to observe all the relevant phenomena. The N×N reference auto-spectral matrix contains all the spectral relationships between individual reference microphones, and is defined as:

$$C_{rr} = E[\vec{r}^* \vec{r}^T], \tag{1}$$

where $\vec{r}$ is the N×1 vector of observed complex sound pressures at the reference transducers and E represents the expectation operator. On a scan-by-scan basis, a vector $\vec{p}$ is also acquired at M hologram, or response, microphones. The M×M response auto-spectral matrix is given as $$C_{pp} = E[\vec{p}^* \vec{p}^T] \tag{2}$$

$C_{pp}$ may be related to the reference auto spectral matrix $C_{rr}$ by the transfer function matrix $H_{rp} = C_{rr}^{-1} C_{rp}$ such that $$C_{pp} = H_{rp}^H C_{rr} H_{rp} \tag{3}$$

Accurate computation of the transfer function matrices when hologram sensors are moving is discussed in greater detail below. $C_{rp}$ is defined as the N×M cross-spectral matrix that relates the reference observations (from reference sensors 130) to the hologram plane observations (from moveable sensors 120). The superscript H refers to the Hermitian, i.e., conjugate transpose operator. Over the entire scan, the signals measured by the reference microphones form a basis for the decomposition of the hologram partial fields. This basis is identified by performing a singular value decomposition on $C_{rr}$ averaged over the entire scan:

$$C_{rr,avg} = U_{avg} \Sigma_{avg} V_{avg}^H = U_{avg} \Sigma_{avg} U_{avg}^H \tag{4}$$

The subscript avg refers to the average value taken over all the individual scans. The matrices U and V are unitary (i.e., $UU^H = U^H U = I_N$) and contain the left and right singular vectors of the decomposition. In this case U=V because $C_{rr}$ is a positive semi-definite Hermitian matrix. Each singular vector is associated with a singular value in the diagonal matrix $\Sigma$, which contains the always positive singular values. The values in $\Sigma$ are ordered from high to low and give an indication of the relative strengths of the decomposed principal components. The inner product of a given singular vector with the vector of observations effectively defines a "virtual" sensor that is individually phase coherent with the partial field associated with its singular value.

A single spatially coherent sound field observed by N microphones has only one non-zero singular value. In the presence of experimental noise the other singular values would be small but non-zero. When a number of mutually incoherent phenomena are present, the number of non noise-related singular values equal the number of relevant phenomena. For any multiple, partially correlated noise sources, it is necessary that the number N be greater than the number of independent phenomena that are being observed. For a turbulent jet, the phenomena may be frequency dependent, with the number of independent modes expected to increase with decreasing characteristic length scale. It has been shown that while more than 350 hydrodynamic modes are necessary to capture only 50% of the flow fluctuation energy, a mere 24 acoustic modes can resolve 90% of the far-field acoustics. This sheds light on the number of reference transducers one may need to perform scan-based acoustical holography on a jet.

The complex stationary acoustic field, or "partial field", $\hat{P}$, that is decomposed by scan-based holography measurement is then given by $$\hat{P} = H_{rp,scan}^T U_{avg}^* \Sigma_{avg}^{1/2} = [U_{scan} \Sigma_{scan}^+ U_{scan}^H C_{rp,scan}]$$
$$\phantom{\hat{P}} ^T U_{avg}^* \Sigma_{avg}^{1/2}, \tag{5}$$

where the auto-spectral matrix $C_{pp}$ must satisfy Equation 2. The subscript scan refers to the value of each individual matrix during each scan while the superscript+ refers to the generalized inverse of the singular value matrix which is obtained by setting to zero all of the singular values assumed to be unrelated to the physical phenomena being observed. Using Equation 5 a set of scans can be sewn together like a patchwork quilt to produce a phase-locked acoustic hologram for each singular value.

The interpretation of these partial fields involves complex stationary acoustic field decomposition using multi-reference acoustical holography. Partial fields are calculated by singular value or eigenvalue decomposition of the cross-spectral matrix, i.e., the matrix of cross-spectra between all channels.

Partial fields do not, in general, correspond to physical phenomena. However, partial fields can be used to project the measured data on the holography plane to other points in the source-free region (i.e., regions not scanned by sensors 130). Furthermore, as the first partial field becomes more dominant (i.e., its singular value becomes much greater than the next largest one), the partial field begins to approximate the effect of the real physical sound field. The computed partial fields are not unique, but serve as a decomposition into coherent fields that satisfy the assumptions of acoustical holography. Parameters that are computed from acoustical holography processing may then be combined, either linearly, or in an RMS sense to obtain total field properties. The notions of singular value decomposition and eigen-decomposition are equivalent and do not change the conclusions presented here. Inspection of the dominant partial fields is valuable to obtain physical understanding, but each partial field is not a coordinate system-independent physical entity. The most relevant partial field is the dominant one. It gives the most physical insight when its eigenvalue is well separated from the others.

A "partial field" is a rank one field multiplied by a complex random variable, making it mutually incoherent with any other partial field. The total acoustic field can be described by the sum of a set of mutually incoherent partial fields. One may construct an acoustic field, recorded at a number of discrete locations, as a sum of mutually incoherent coherent fields as in:

$$P = \sum_{k=0}^{N} P_k \alpha_k, \tag{6}$$

where the vector P is the total field, $P_k$ is a constant vector (observed at a given set of locations) and $\alpha_k$ is a complex random scalar such that:

$$E\alpha_i \bar{\alpha}_j = 0, \text{ for all } i \neq j, \tag{7}$$

meaning that the scalars are mutually incoherent.

For any index k, the partial field given by the random vector $P_k \alpha_k$ is a coherent pressure field upon which the normal methods of acoustical holography can be applied to project both to the far field and towards a surface enclosing the source.

The matrix of all spectra is then $$G_{PP} = E(PP^H) = \sum_{k=0}^{N} P_k \bar{P}_k \sigma_k^2, \quad (8)$$

with $$\sigma_k^2 = E(\alpha_k \bar{\alpha}_k).$$

One special case corresponds to unweighted partial fields. The spectral matrix $G_{PP}$ of Equation 8 is Hermitian, so it has an eigen-decomposition:

$$G_{PP} = V \Lambda V^H, \quad (9)$$

with a diagonal matrix of eigenvalues $\Lambda = \{\lambda_k\}$, and an eigenvector matrix $V = (\ldots V_k \ldots)$. The eigenvectors are mutually orthogonal, i.e., $V^H V = I$. It follows that the spectral matrix $G_{PP}$ could have been generated by a pressure field written as $$\tilde{P} = \sum_{k=0}^{N} V_k \beta_k, \quad (10)$$

where $$E(\beta_k \bar{\beta}_k) = \lambda_k.$$

Each such $V_k \beta_k$, where $\beta_k$ is a complex random scalar, is a coherent field, and we can apply the projection methods of acoustical holography to extend this field toward and away from the source. The total extended field is then clearly the sum of these fields.

It should be noted that the eigenvectors $V_k$ are mutually orthogonal, whereas the same cannot be said about the partial fields $P_k$ of Equation 6. The physical interpretation of the partial fields $V_k$ should therefore be taken with some reservations; their value lies in that they provide partial fields that are amenable to acoustical holography and sum up to the total field.

Often, instead of a complete autospectral matrix, we may be considering a submatrix of $G_{PP}$ obtained by selecting a crossspectral matrix $G_{PS}$ where S is a subset of the channels in P. Instead of an eigen-decomposition we will use a singular value decomposition $$G_{PS} = \tilde{V} \Sigma \tilde{U}^H, \quad (11)$$

where $\tilde{V}$ and $\tilde{U}$ are matrices with unitary columns (mutually orthogonal), and $\Sigma$ is a quasi-diagonal matrix of non-negative singular values. The partial fields are then represented by the columns of $\tilde{V}$. In the special case where P=S, Equation 11 reduces to Equation 9.

One can extract eigenvectors (partial fields) in any way, and they will be directly amenable to acoustical holography computations, which may then be subsequently superposed linearly (projected towards and away from the source). On the other hand, visualization of the dominant partial field(s) gives valuable insight into the nature of the dominant coherent phenomena at a given frequency as long as we understand that the computed fields are linear combinations of the underlying physical sources.

For shock-containing military jets, preliminary sizing estimates based upon typical aircraft engine jet geometries and documented array spacing suggests that meeting the highest frequency requirements of interest (O[20 kHz]) by generating conventional holograms over a typical hologram plane is impractical. For example, others have presented data at 1 kHz using 16 scanning and 48 reference microphones in a cylindrical arrangement for a 0.8 cm burner nozzle jet source operating at Mach 0.26. Array microphones are scanned at axial increments of 3.0 cm (about 11 points per 1 kHz wavelength), and a circumferential (arc) spacing of 6.0 cm, (about 6 points per 1 kHz wavelength). When scaled to 20 kHz, this corresponds to a point spacing of roughly 3 mm, requiring about $10^5$ scans over the entire assumed source plane. For data records in the range of 1 to 20 seconds, this might correspond to anywhere between 30 and 600 hours for data acquisition. Hence it is crucial to reduce the number of scan points.

In accordance with certain embodiments, two signal processing techniques are used as a means to reduce both scan time and sensor count. First, transfer functions are constructed at points in space between continuously moving microphones and fixed reference transducers. The methodology includes averaging capability by employing Chebyshev spacing of points upstream and downstream of the point of interest as the microphone passes through. Second, a more efficient computation of spatio-temporal transfer functions includes canonical coherences that uses all spectral data to narrow the state space down to the area where one only looks at the phenomena that are mutually coherent between the references and the response transducers.

As previously mentioned, some stationary measurement situations entail the phase correct estimation of spectral matrices for a large number of transducers locations distributed over a geometry or test subject. Quite often, it is infeasible to measure all locations simultaneously due to financial or physical constraints. Stationarity allows one to perform measurements at arbitrary time points; but in order to obtain phase coherency between data sets acquired at different instants of time, the system must be able to estimate transfer functions between a fixed set of transducers and the roving transducers at any desired position of the roving transducers.

Current approaches to roving acquisition use a robot to perform a series of moves to fixed locations and dwell there until sufficient averaging has taken place. The start and stop motion induce vibration transients, which add to the appreciable amount of time expended averaging. In contrast, the present invention involves continuously moving transducers with, for example, real time position feedback. The assumption is that the transfer functions are smooth functions of position which allows the system to use averaging information in a geometric neighborhood of each desired measurement location. The smoothness assumption put limits on the scan speed to a required degree of averaging. It is worth noting that continuous motion results in much smaller vibration and positioning transients than the traditional start and stop scheme.

Figure 2:
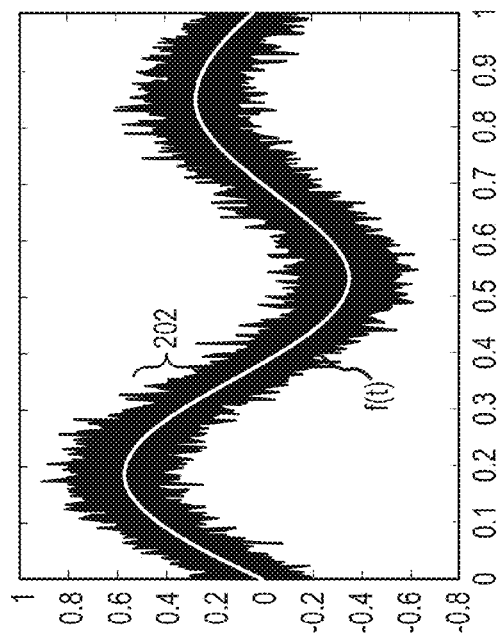
FIG. 2 is graph depicting an oscillatory function useful in describing the present invention.

Referring to FIG. 2, consider the estimation of a function $f(t)$ which is defined on the interval [0 1]. The function has a certain oscillatory nature. In this example, the function may be measured at any position, but with a random measurement error 202 as shown. To avoid aliasing of data, the sampling theorem states that the system must sample faster than twice per wave length. In this experiment, then, assume the system will sample the noisy data at a set of locations within this interval in order to estimate an accurate value of the underlying function at enough points to avoid aliasing.

Expand the function to be estimated into a finite sum of Chebyshev polynomials $T_n(t)$, as shown in FIG. 3. The mathematical expression is then:

$$f(t) = \sum_{n=0}^{N} c_n T_n(t) + \varepsilon(t), \qquad (12)$$

where $\varepsilon(t)$ is the error, consisting of estimation error and possible lack of fit to the finite set of Chebyshev basis functions. The Chebyshev polynomials are selected in this case since any continuous function can be uniformly approximated with the basis of Chebyshev polynomials. Also, if the underlying function possesses a modicum of smoothness, the rate of convergence will be exponential, unlike polynomial approximations. A reasonably optimal selection of sampling points for a given number N+1 of sampling points is:

$$t_k = 0.5\left(1 - \cos\left[\frac{(2k+1)\pi}{2(N+1)}\right]\right) \qquad (13)$$
$$k = 0, 1, \cdots, N,$$

which is seen to have an uneven spacing of the interval with a higher density at either end. The corresponding interpolating function is given by:

$$F(t) = \sum_{n=0}^{N}{}' c_n T_n(t), \qquad (14)$$

where the prime notation on the sum means that the first term $c_0 T_0$ should be divided by 0.5. The interpolation coefficients are given by:

$$c_n = \frac{2}{N+1} \sum_{k=0}^{N} \tilde{f}(t_k) T_n(t_k), \qquad (15)$$

where $\tilde{f}(t_k)$ is the measured function, including measurement noise.

Figure 4:
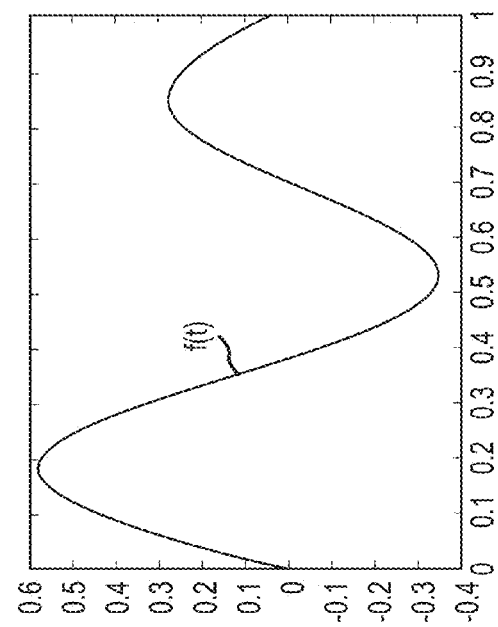
FIG. 4 is a graph depicting a low wavenumber function associated with FIG. 2.

If N+1 sampling points are used, and the underlying function is smooth enough to be approximated by the first K+1 terms, then, by using the estimate:

$$F^K(t) = \sum_{n=0}^{K}{}' c_n T_n(t), \qquad (16)$$

it can be seen that an effective averaging comparing to N−K samples results, with a standard deviation shrinking with $$\frac{1}{\sqrt{N-K}}$$

as the number of sampling points grows. There is a pragmatic statistical upper limit to the number of sampling points since it is desirable that the error in adjacent sampling points be uncorrelated for effective averaging. FIG. 4 demonstrates that the underlying low wavenumber function can be well approximated using only a few (8) Chebyshev polynomials, despite the presence of noise shown in FIG. 2. It will be appreciated that the horizontal axes of FIGS. 2, 3, and 4 correspond to time (normalized or non-normalized), and similarly the vertical axes of those figures correspond to normalized or non-normalized measurements, such as acoustic pressure.

If the sensor position is parameterized as a function of elapsed time, then, for any time point with its corresponding position we may construct a small interval around that time point where the underlying function will have a limited number of cycles, preferably only a segment of a cycle. The estimation of Chebyshev expansion coefficients gives us then an interpolation function which may be evaluated to give us an averaged estimate at the center point. Inspection of the derivation of the estimation procedure tells us that the function to be estimated need not be a scalar, it may also be any tensor or matrix, such as a matrix of spectra and cross spectra.

This approach gives us a very high resolution of spectral estimation along a path of robotic motion. To achieve sufficient resolution on a surface, however, the paths must be close enough that we can interpolate without aliasing between paths. Unless additional assumptions are used, the distance between scan lines must be less than half the wavelength in the direction normal to the scan lines. Our scan patterns are therefore better interpreted as parallel lines in some curvilinear geometry rather than giving rise to a regular set of cells.

The following section describes transfer function estimation through canonical coherence analysis. The goal is to estimate transfer functions between a fixed set of reference transducers and a set of roving response transducers at an arbitrary point on the scan path. It is important to note that these transfer functions are a function of geometry as well as of the stationary field that we have measured, so that we understand that we are describing correlation, but not causality. The reference sensors 130 are preferably chosen so as to capture all or substantially all coherent phenomena of the field in question, such that knowing the field at the reference transducers, the system can construct the corresponding field at all the response transducer point with the help of the transfer functions.

Typically, the system should include at least as many reference sensors 130 as there are mutually incoherent sources in the field. Since different frequency bands tend to have a different number of sources, and also some sources are not measurable at all transducer locations, it is desirable to include a redundant set of reference transducers. This redundancy leads to numerical problems in the conventional algorithms used for transfer function estimation.

For this example, denote the random vector of reference transducers at a given frequency by X, and the random vector of response transducers by Y. The spectral matrices that are acquired are defined as:

$$G_{XX} = E(XX^H),\ G_{XY} = G_{YX}{}^H = E(XY^H),\ \text{and}\ G_{YY} = E(YY^H), \qquad (17)$$

where the expectation operator $E(.)$ is approximated by averaging in the statistical sense.

The transfer function is defined as a matrix H, such that:

$$Y = HX, \qquad (18)$$

and by postmultiplying by $X^H$ and taking expectations we receive:

$$G_{YX} = HG_{XX} \tag{19}$$

Solving for the transfer function H:

$$H = G_{YX} G_{XX}^+, \tag{20}$$

where the plus sign denotes a suitable generalized inverse. The autospectral matrix $G_{XX}$ the references is positive semi-definite hermitian and square, but is typically numerically ill conditioned, such that traditional estimation techniques find a generalized inverse by singular value decomposition (SVD), or other regularization techniques. Inspection of the traditional solution also shows that $G_{YY}$ is not being used, which means that the information in parts of the acquired data is being ignored.

We shall construct two sets of vectors, $\alpha_i$ and $b_i$, such that the random scalars $\alpha_i^H X$ and $b_j^H Y$ are incoherent for $i \neq j$ and the coherence between $\alpha_i^H X$ and $b_i^H Y$ is not less than the coherence between $\alpha_j^H X$ and $b_j^H Y$ for all $i < j$. The solution is found by solving the eigenvalue problem:

$$G_{XX} \alpha \lambda = G_{XY} G_{YY}^+ G_{YX} \alpha, \tag{21}$$

where the generalized inverse is any that satisfies $A = AA^+ A$. Select $\alpha_i$ as an eigenvector which corresponds to a non zero and finite eigenvalue $\lambda_i$, and sort the eigensolutions such that $\lambda_i \geq \lambda_j$ for $i < j$. The corresponding $b_i$ vectors are given by $G_{YY}^+ G_{YX} \alpha_i$. The coherence between $\alpha_i^H X$ and $b_i^H Y$ is $\lambda_i$ and is called a canonical coherence. We normalize the eigenvectors such that $\alpha_i^H G_{XX} \alpha_i = 1$, which implies that $\alpha_i^H G_{XY} G_{YY}^+ G_{YX} \alpha_i = \lambda_i$.

The derivation of this method is based on arguments associated with the optimization of Rayleigh quotients. It can be shown that the same solutions may be found by interchanging the roles of X and Y even when the two sets of transducers are of a different size.

By mapping the physical transducer measurements into canonical coordinates $x_i = \alpha_i^H X$ and $y_i = b_i^H Y$, the task of estimating transfer functions is reduced to finding an optimal scalar transfer function for each canonical coordinate, whereupon we may transform back to the physical coordinates.

It can shown that the spectral matrix of:

$$\begin{Bmatrix} x_i \\ y_i \end{Bmatrix} \text{ is } \begin{pmatrix} 1 & \lambda_i \\ \lambda_i & \lambda_i \end{pmatrix}.$$

The standard estimates are then:

$$H_1 = \lambda_i, \tag{22}$$

$$H_2 = 1, \text{ and} \tag{23}$$

$$H_v = \sqrt{H_1 H_2} = \sqrt{\lambda_i} \tag{24}$$

It is well known in practice from structural modal analysis that the $H_1$ is optimal when there is no noise on the input, the $H_2$ is optimal when there is no noise on the output, and that $H_v$ is optimal when there is noise on both references and responses. We shall therefore choose $H_v$ as given by Equation 24. It can be shown that $|H_1| \leq |H_v| \leq |H_2|$.

With the normal scaling convention, it can be shown that $b_i^H G_{YY} b_i = \lambda_i$, so that the mapping from the physical reference to canonical coordinate i through the $H_v$ transfer functions and then to the physical response is given by:

$$\lambda_i^{-1} G_{YY} G_{YY}^+ G_{YX} a_i \sqrt{\lambda_i} \, a_i^H = \lambda_i^{-\frac{1}{2}} G_{YY} G_{YY}^+ G_{YX} a_i a_i^H. \tag{25}$$

Equation 25 shows the transfer function for canonical coordinate number i, so it follows by combining all nonzero canonical coordinates that the total transfer function is:

$$G_{YY} G_{YY}^+ G_{YX} A \Lambda^{-\frac{1}{2}} A^H, \tag{26}$$

where $\Lambda$ is the diagonal matrix of nonzero finite eigenvalues of Equation 21 and A is the column matrix of the normalized eigenvectors. This transfer function estimate uses sufficient statistics, i.e., does not ignore the information in $G_{YY}$, and is also robust in the presence of noise both on the references and the responses. Another benefit is that failed transducers among the references will be ignored since they cannot be coherent with any other transducer in the responses.

EXPERIMENTAL SETUP

Experiments relating to the conceptual diagram of FIG. 5 were conducted in a facility that uses a Kaeser air compressor to pressurize two 18.9 m³ tanks to a pressure of 1.34 MPa (195 psig). The compressed air passes through a dryer and is then piped to a plenum before exhausting through a model nozzle for point source 506 in the facility's anechoic chamber. Nozzle diameters up to 1 inch (0.0254 m) are typically used, though the experimental results presented herein focus on a 0.7 inch (0.0178 m) diameter jet.

Inside the anechoic chamber, fiberglass wedges are attached to each wall, resulting in chamber wedge-to-wedge dimensions of 5.02×6.04×2.79 m (16.5×19.82×9.15 ft) and a cutoff frequency of 250 Hz. An exhaust system, beginning on the wall opposing the plenum, ingests the flow in order to maintain approximately constant ambient conditions inside the chamber.

A robotically controlled acoustical holography array (e.g., 120 and 503) takes measurements in the hydrodynamic and/or acoustic near-field of laboratory-scale jets in the facility. The array consisted of an approximately 4 ft (1.22 m) long boom that holds twelve Bruel and Kjaer (B&K) 4944A microphones. These twelve array (i.e. "hologram") sensors are spaced 4 inches (10.2 cm) apart in a straight line, as pictured in FIG. 5

The boom 503 is connected to a linear track that allows it to move in the direction aligned with the microphones. The boom and linear track are mounted on a bracket assembly that is in turn held by a machined cylinder mounted on a bearing around the jet (not shown). A toothed gear around the cylinder is connected to another motor to allow the entire assembly to rotate. Therefore the array of microphones can be moved in two degrees of freedom, translational (along the sensor line) and rotational. Additionally, a pin allows the bracket assembly to be set at a range of arbitrary angles relative to the jet centerline, allowing data to be acquired on conical or cylindrical surfaces. Microphone orientation is defined in a cylindrical coordinate system relative to the center of the nozzle with the microphone closest to the jet located at approximately 2¼ inches (5.7 cm) axially from the jet nozzle exit plane and 2 inches (5.1 cm) radially from the jet centerline in the conical configuration.

The full acoustical holography experiment contains 24 B&K 4944A reference microphones located on three linear arrays of eight microphones. Thus the total number of microphones in the experiment equals 36. The reference microphone arrays were assembled using supports constructed of perforated angles and covered with acoustic foam.

Full scans were conducted over a 315 degree arc on the hologram surface. The 45 degree sector located right below the jet was a "no-scan" zone due to array stop requirements. Stationary microphone ("fixed-index") acquisitions were taken at spacings of one inch (2.54 cm) in the array translation direction and 22.5 degrees in the circumferential direction. Therefore each microphone in the array visited a total of 60 points (4 linear×15 circumferential), for a total fixed-index grid of 48×15 points. Additionally, moving scans were taken through each line of translational and circumferential grid points. Linear scans were taken at a speed of 1.0 cm per second, while moving scans were taken at 12 degrees per second.

A point source (506) was also constructed from a midrange speaker in an enclosure and connected to a long flexible tube with a nozzle at the end in order to validate the continuous scan technique on a sound source with near-perfect spatial coherence before examining acoustic holograms obtained from jets. In subsequent paragraphs, results are presented for both acoustical holography scans of the point source and of a supersonic, imperfectly expanded jet with a strong screech tone.

The results suggest that the techniques described above allow the system to measure high-resolution acoustic holograms of the dominant partial field of a noise source. Two examples are described: a point source that emits a strong, spatially coherent tone, and an imperfectly expanded supersonic jet. Data are presented for stationary hologram acquisitions taken on a fixed-index grid as well as continuously moving microphone acquisitions taken along a single line in the array translational direction.

Experiment 1

Figure 6:
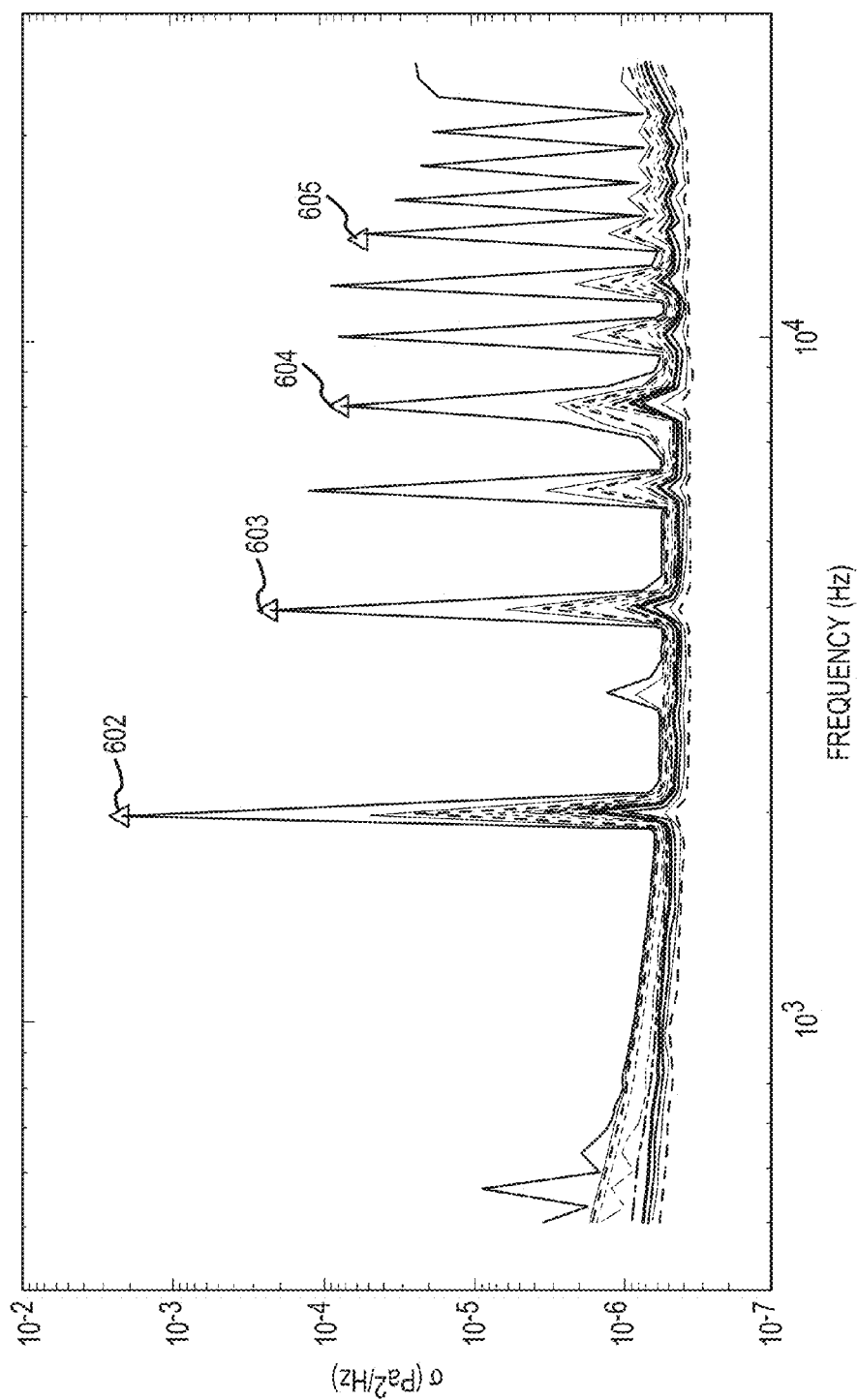
FIG. 6 is a graph depicting singular values of a reference auto-spectral matrix for a point-source scan.

In accordance with the present invention, a point source 506 was scanned with the jet nozzle 516 turned off. The end of the point source nozzle was located about 14 inches (35.6 cm) downstream of the jet nozzle exit plane, as pictured in FIG. 5. A full scan of grid points was made over an 8 inch (20.3 cm) radius cylindrical surface around the point source located near the 14 inch (35.6 cm) axial coordinate (i.e., with the boom 503 of FIG. 5 positioned parallel to axis 502). The point source produced a strong 2.0 kHz tone with higher harmonic frequencies, as indicated by the singular values of $C_{rr}$ plotted as a function of $\frac{1}{2}^{th}$ octave band frequency in FIG. 6 Note that the amplitude of $C_{rr}$ at each frequency is converted to a spectral density in this figure, so the singular values have units of Pa²/Hz. The triangular symbols (602-605) shown on the highest singular value at 2.0, 4.0, 8.0 and 14.0 kHz represent the dominant partial fields at those frequencies.

Figure 7:
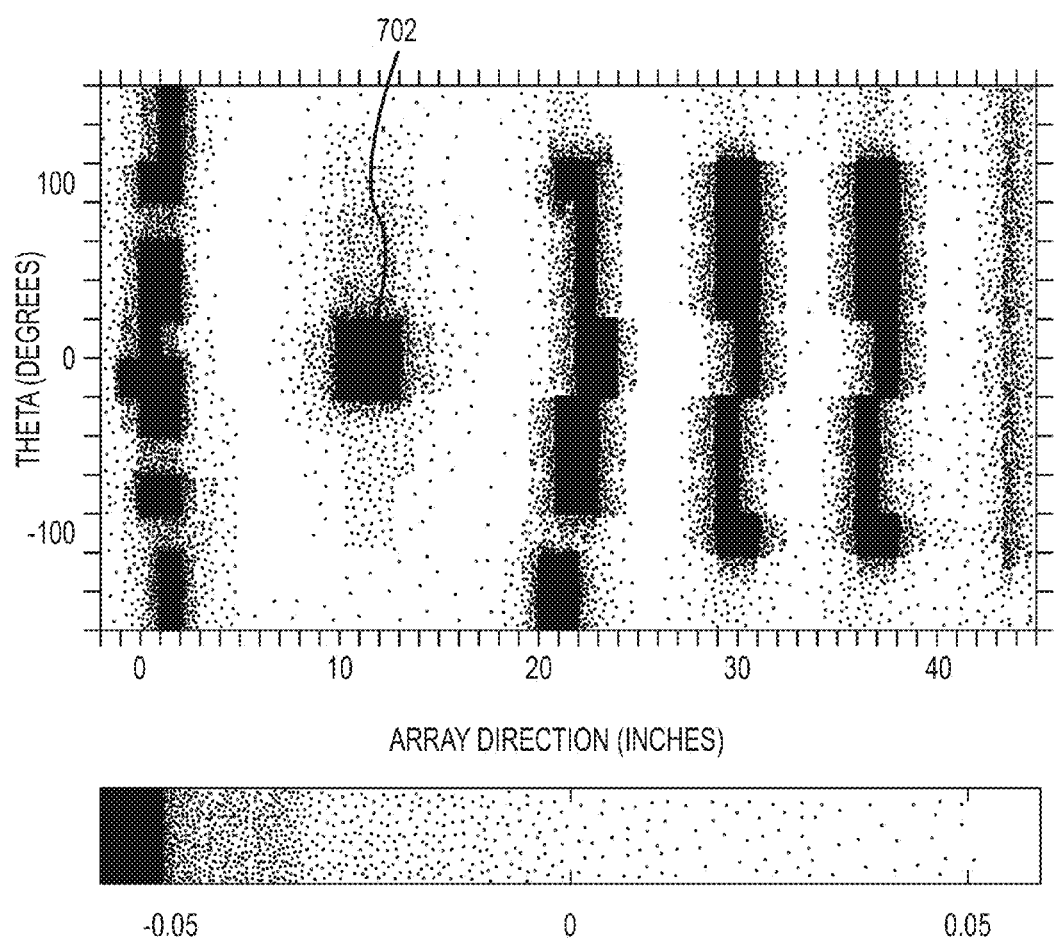
FIG. 7 is a 2D unwrapped representation of a dominant partial field for a point-source.
Figure 8:
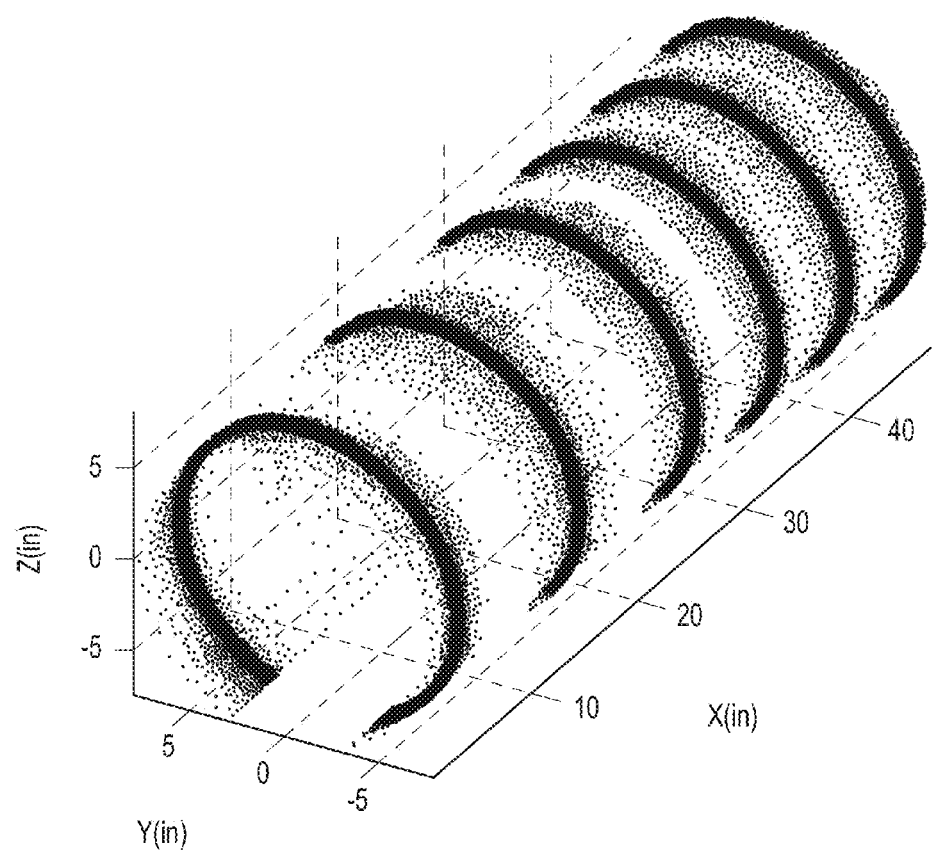
FIG. 8 is hologram cylinder corresponding to the 2D representation of FIG. 7.
Figure 10:
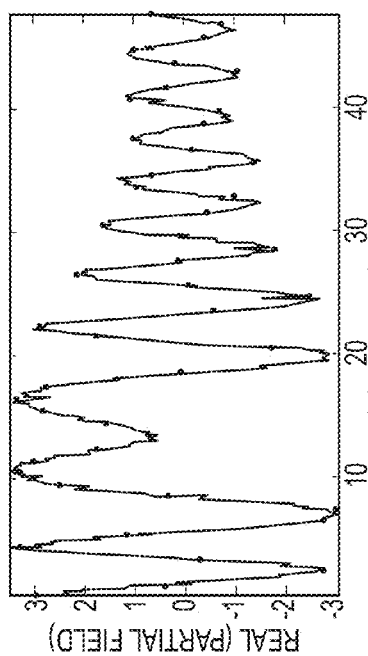
FIG. 10 is a graph as shown in FIG. 9 in accordance with a 4 kHz tone.
Figure 9:
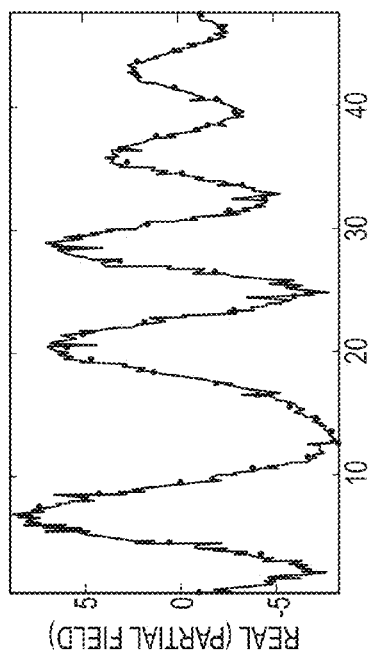
FIG. 9 is a graph depicting the real part of a dominant partial field in accordance with a 2 kHz tone.
Figure 12:
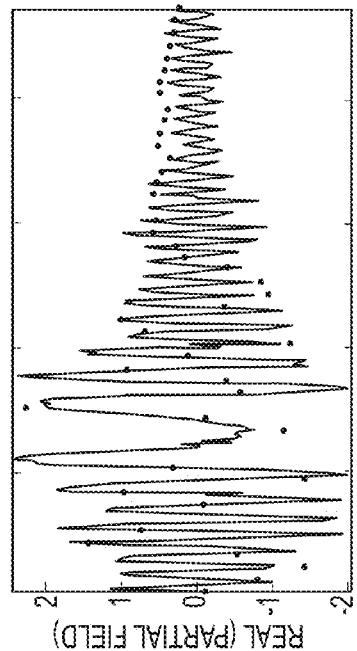
FIG. 12 is a graph as shown in FIG. 9 in accordance with a 14 kHz tone.
Figure 11:
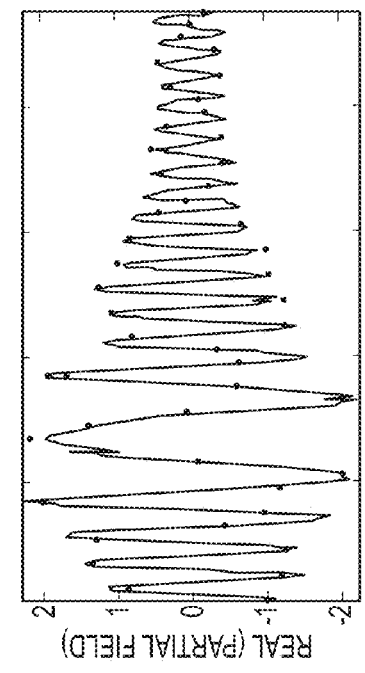
FIG. 11 is a graph as shown in FIG. 9 in accordance with a 8 kHz tone.

FIG. 7 presents the real part of the dominant complex partial field at 2 kHz over the entire fixed-index grid with spacing of one inch (2.54 cm) in the array direction and 22.5 degrees in the circumferential direction. Specifically, FIG. 7 presents the partial field in a two-dimensional projection in the translational (abscissa)-circumferential (ordinate) plane. The same partial field is shown in FIG. 8 on the cylindrical hologram surface. The origin of the coordinate system is the center of the nozzle 506 shown in FIG. 5, with the jet axis in the positive x-direction and the vertical axis in the positive z-direction.

The ovoid shape 702 in the planar representation of the partial field (FIG. 7) is centered around the location of the point source, and shows that there is some angular variation of the amplitude and phase of this dominant partial field. This is mostly due to the fact that the sound source used in the test is only an approximate point source, but might also be due to some slight misalignment of the scanning array.

The wavefronts show that the magnitude decays away from the point source axial station and the obtained wavelength is consistent with the expected wavelength of sound of this frequency traveling at the ambient sound speed. Since the field is complex it can be animated by multiplication by a time harmonic function $e^{i\omega t}$. The arrows indicate that the partial field measurement is able to capture the propagation direction of the acoustic waves: away from the point source in this example.

FIGS. 9-12 present the real part of the measured dominant partial field at 2 kHz, 4 kHz, 8 kHz, and 14 kHz, respectively, along a continuous line parallel to the axis of the hologram cylinder and directly above the point source 506 (i.e. θ=0°). Circular points indicate data acquired from microphones during stationary acquisitions, while the dark lines represent the constructed partial field from the continuously moving array.

For the stationary scans, measurement locations were spaced one inch apart, implying that the spatial Nyquist frequency based on two points per wavelength is 6.7 kHz. At frequencies above this value it would be expected that the stationary scans would result in aliasing of data, which is clear from the data in FIGS. 11 and 12. The partial field values obtained from the continuous scan fits fairly closely to the ones obtained with the fixed scan, with only small discrepancies between the magnitude of the two. Thus it can be inferred that the continuously moving microphone transfer function estimation technique can increase spatial resolution with a fixed number of sensors that would otherwise be constrained by their microphone spacing or their array aperture size.

Experiment 2

Figure 13:
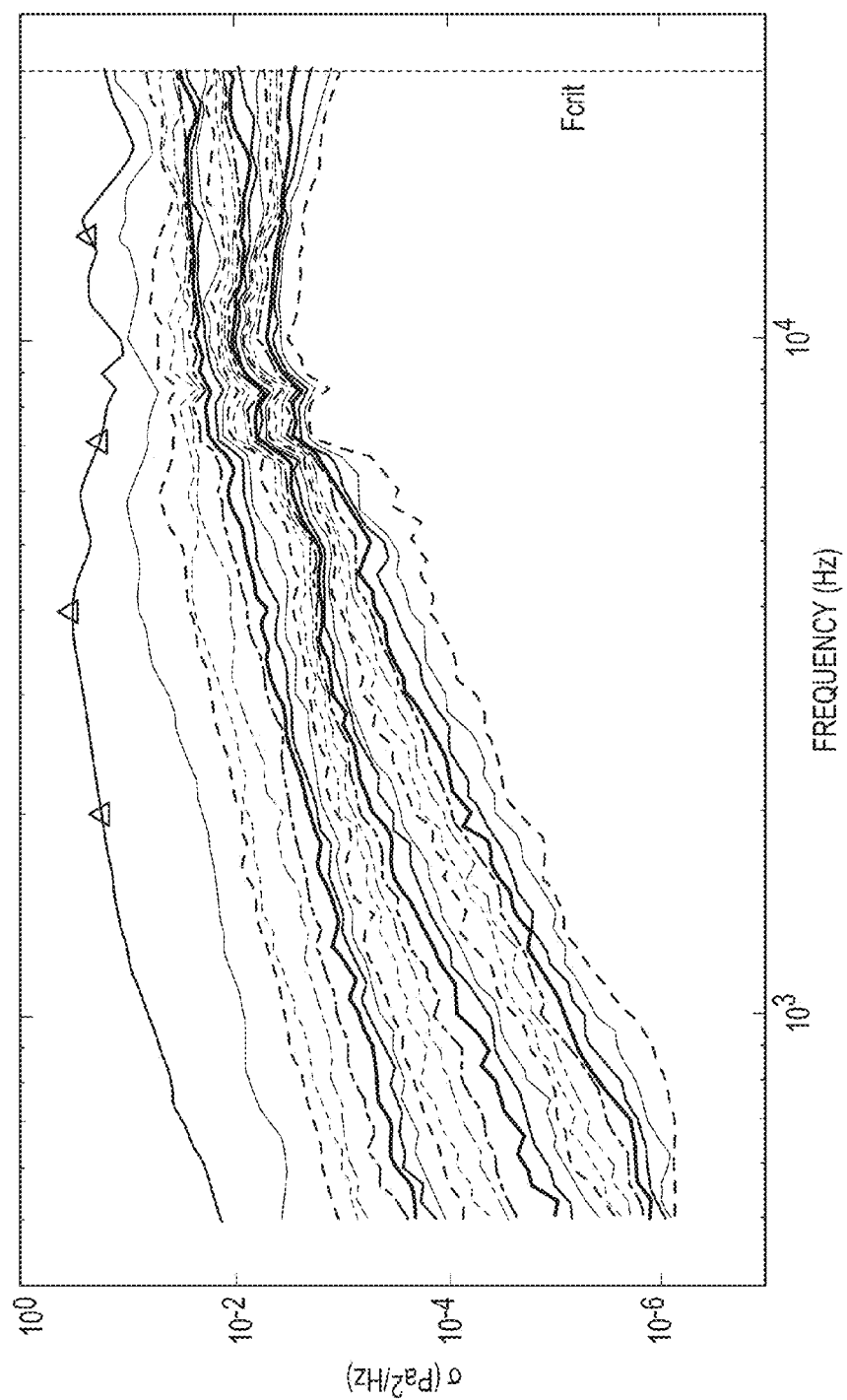
FIG. 13 is a graph depicting singular values of a reference auto-spectral matrix for a shock-containing jet scan in accordance with one embodiment.

A 0.7 inch (1.78 cm) jet nozzle with design Mach number ($M_d$) of 1.3 was run in an underexpanded state with a stagnation to ambient nozzle pressure ratio corresponding to a perfectly expanded jet Mach number ($M_j$) of 1.5. The holography array was set at a 10 degree half angle to sweep a conical surface, as pictured in FIG. 5. The same types of scan were performed on the supersonic jet as on the point source described above. FIG. 13 presents the singular values of $C_{rr}$ as a function of $\frac{1}{12}^{th}$ octave center frequency. Again, as with the point source, the singular values are presented in units of spectral density, i.e., Pa²/Hz. The critical frequency associated with a Strouhal number of unity is indicated by the dashed vertical blue line, and corresponds to approximately 25 kHz. Data are shown in this section for the dominant partial field associated with the triangular symbols at 2.0, 4.0, 7.1, and 14.2 kHz. It is worth noting that the dominant singular value is as much as an order of magnitude larger than the second singular value at certain low frequencies. Also, over most frequencies the first four to six singular values appear to be well over an order of magnitude larger than the remaining singular values, suggesting that over 90% of the acoustic energy can be described by these few associated partial fields. At lower frequencies the noise mechanism is understood to be due to instability waves associated with large turbulence structures, while the hump that peaks near 14 kHz is broadband shock associated noise (BBSAN), as indicated in the figure. The next two figures examine the quality of the data of the dominant partial field for these noise mechanisms.

Figure 14:
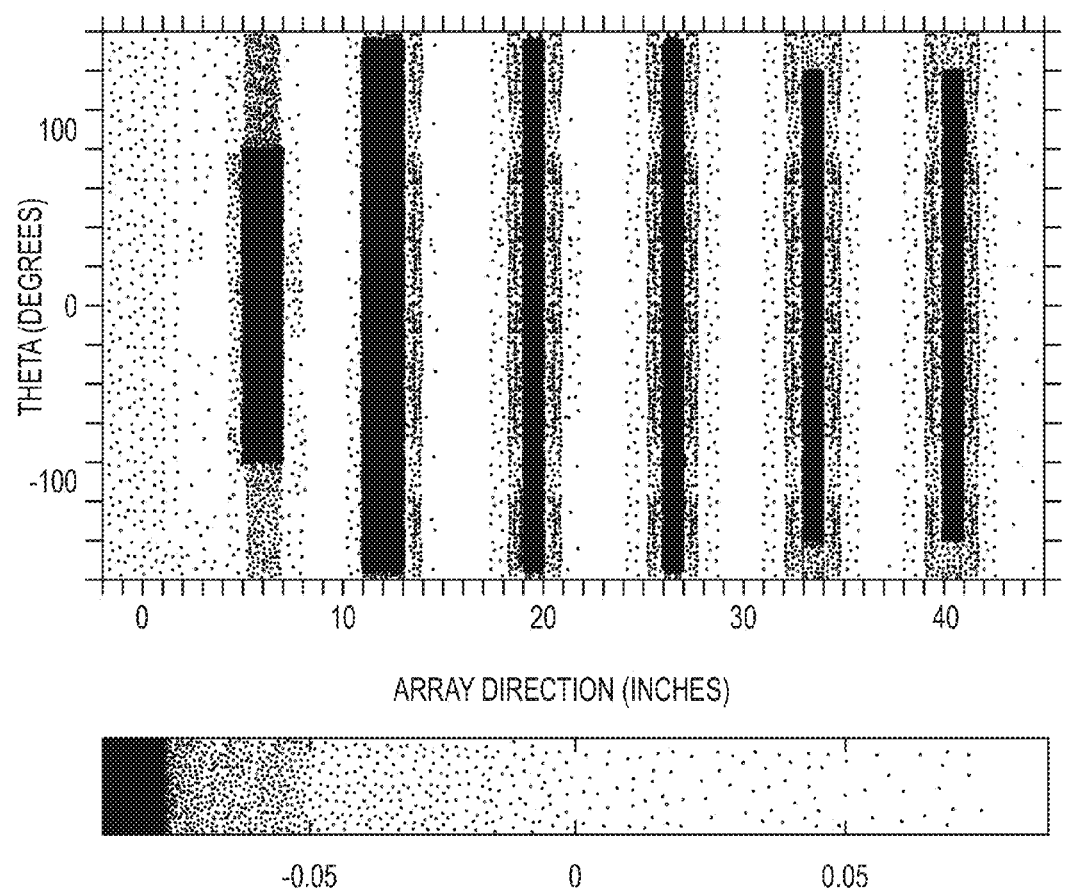
FIG. 14 is a 2D unwrapped representation of a dominant partial field for a shock-containing jet scan in accordance with one embodiment.
Figure 15:
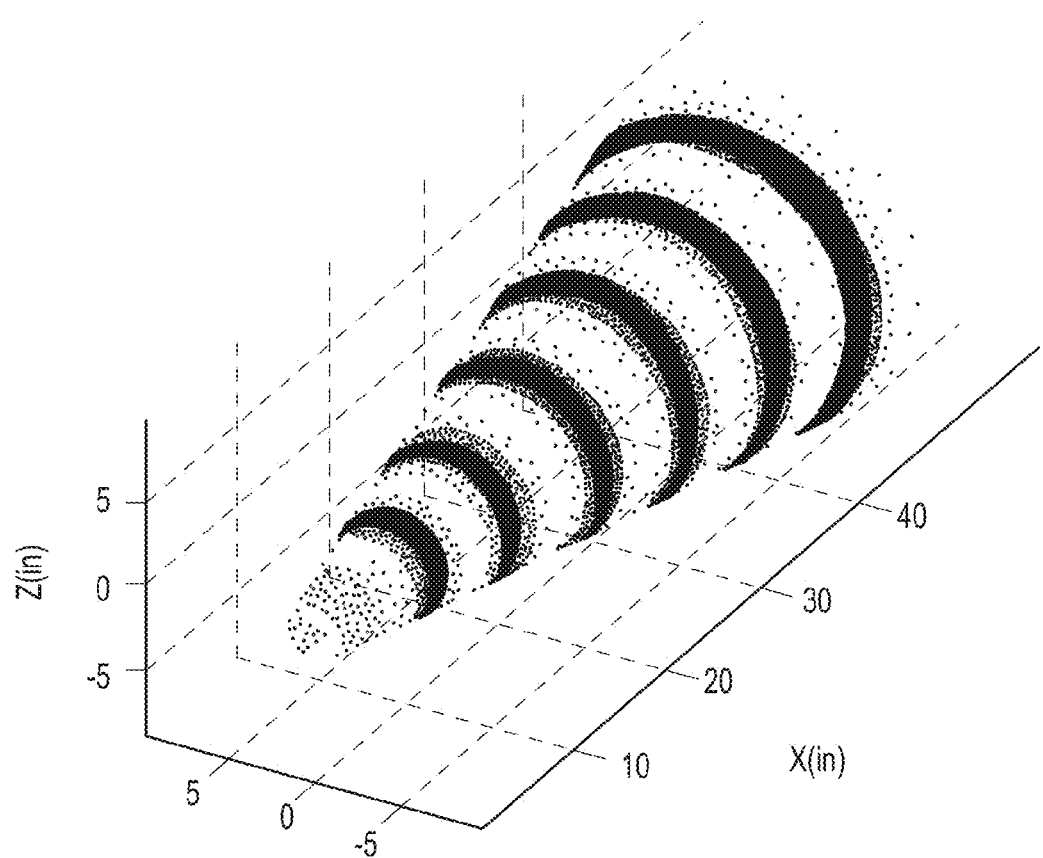
FIG. 15 is a hologram cone corresponding to the representation of FIG. 14.
Figure 16:
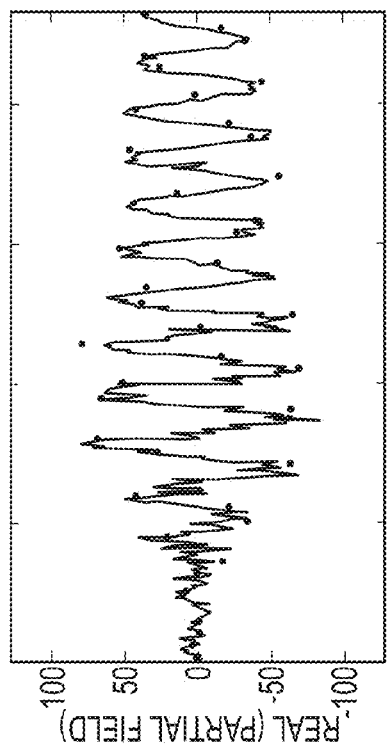
FIG. 16 is a graph depicting the real part of a dominant partial field for shock containing an underexpanded jet at 2 kHz.
Figure 17:
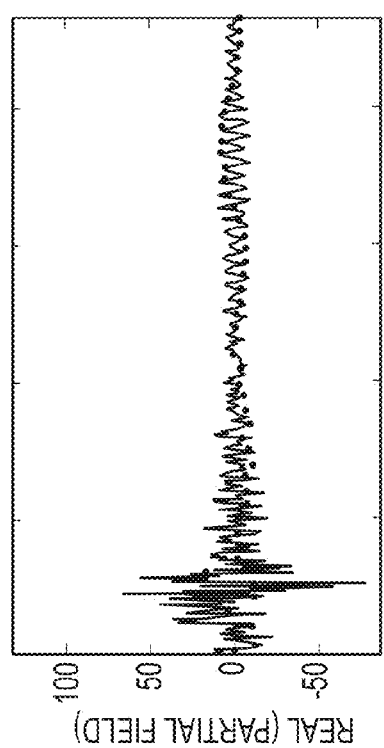
FIG. 17 is a graph depicting the real part of a dominant partial field for shock containing an underexpanded jet at 4 kHz.
Figure 18:
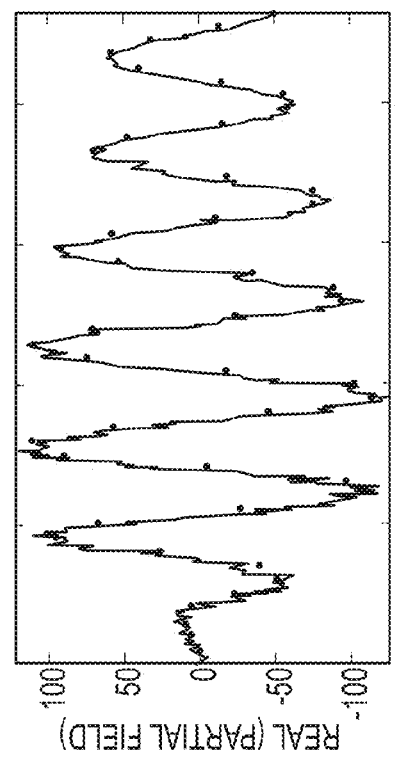
FIG. 18 is a graph depicting the real part of a dominant partial field for shock containing an underexpanded jet at 7.1 kHz.
Figure 19:
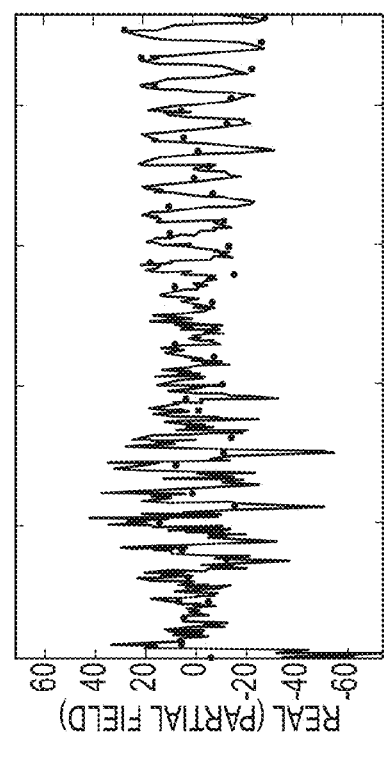
FIG. 19 is a graph depicting the real part of a dominant partial field for shock containing an underexpanded jet at 14.2 kHz.

FIG. 14 shows the real part of the dominant partial field at 2.0 kHz over the 48 axial points by fifteen circumferential points fixed-index grid. FIG. 15 shows the field plotted on the conical hologram surface. The dominant partial field at this frequency corresponds to a Strouhal number of 0.08. The Strouhal number is a dimensionless frequency equal to the product of temporal frequency and fully expanded jet diameter divided by fully expanded jet velocity. The wavelength close to the jet, for x/D<20 is shorter than further downstream, where the microphones are radially and axially more distant from the jet. The dominant noise mechanism at this frequency is associated with large scale turbulent structures convecting within the mixing layer of the jet. Close to the jet, the pressure field is dominated by hydrodynamic pressure fluctuations associated with these convecting turbulent structures. Further away, the wavelength corresponds to acoustic waves propagating through ambient air. Animation of the partial field shows that the wave-like structures convect downstream This can also be seen in the plot of the dominant partial field (real part) obtained along the line θ=−157.5° at 2.0, 4.0, 7.1, and 14.2 kHz shown in FIGS. 16-19. For example, by measuring the wavelength and the temporal frequency for the 2.0 kHz waveform it can be determined that these waves convect downstream near the speed of sound in the acoustic medium far downstream, while close to the jet nozzle these waves relate to convecting turbulent structures that travel at a speed that is roughly 70% of the jet velocity. A similar finding is observed at 4.0 kHz, though the data become noticeably noisier near the nozzle. Finally, the data at 7.1 kHz and 14.2 kHz reveal an entirely different propagation pattern. Far downstream, the propagation speed is still equal to the ambient sound speed, while upstream the waves appear to be standing when animated.

The Use of Vold-Kalman Order Extraction in Continuous Scan Imaging

When dealing with test subjects that include rotating elements of the type that generate a multitude of deterministic or "tonal" acoustic components in addition to random components (e.g., shafts, fans, etc.), it is advantageous to individually identify, separate, and image these tonal components. This extraction process and subsequent imaging method is most commonly performed with respect to different orders, i.e., multiples of the fundamental shaft rotation frequency.

In that regard, as described in detail below, embodiments of the present invention utilize an unconventional formulation of the Vold-Kalman filter for time domain order tracking applied to continuous scan imaging of such subjects. The method allows separation of the deterministic components from the indeterministic components so that the plurality of tonal components may be imaged as individual partial fields. A tachometer sensor (or other suitable rotational sensor) provides a synchronous time history of the rotating element's position, and thus provides phasing information in addition to or in place of the reference sensors as described above. The tachometer effectively serves as an analog for the stationary reference microphones described above and enables imaging of those components. The tonal components (e.g., shaft and fan blade harmonics) are self-coherent sound fields in their own right, and thus their absolute phase relationships to the shaft is provided by the corresponding tachometer signal as a reference. Computation of the partial fields then relies on the response auto-spectral matrix of the movable response sensors and this absolute phase relationship.

Furthermore, in accordance with another embodiment, the accuracy of the imaging technique may be improved through application of a Doppler correction to account for the relative velocity between the sensors and the source, which is advantageous for particularly fast scanning. The formulation used herein extends Doppler correction beyond the conventional implementations to account for multiple shafts and distributed sound sources. The application of Doppler corrections allows extraction of harmonics from distributed sources and multiple shafts and enables the use of higher scan speeds for the movable response sensors. In one embodiment, the broadband components of the sound field are not linked coherently to the shafts, such that in order to extract self-coherent partial fields for these, stationary reference microphones are still employed.

Figure 21:
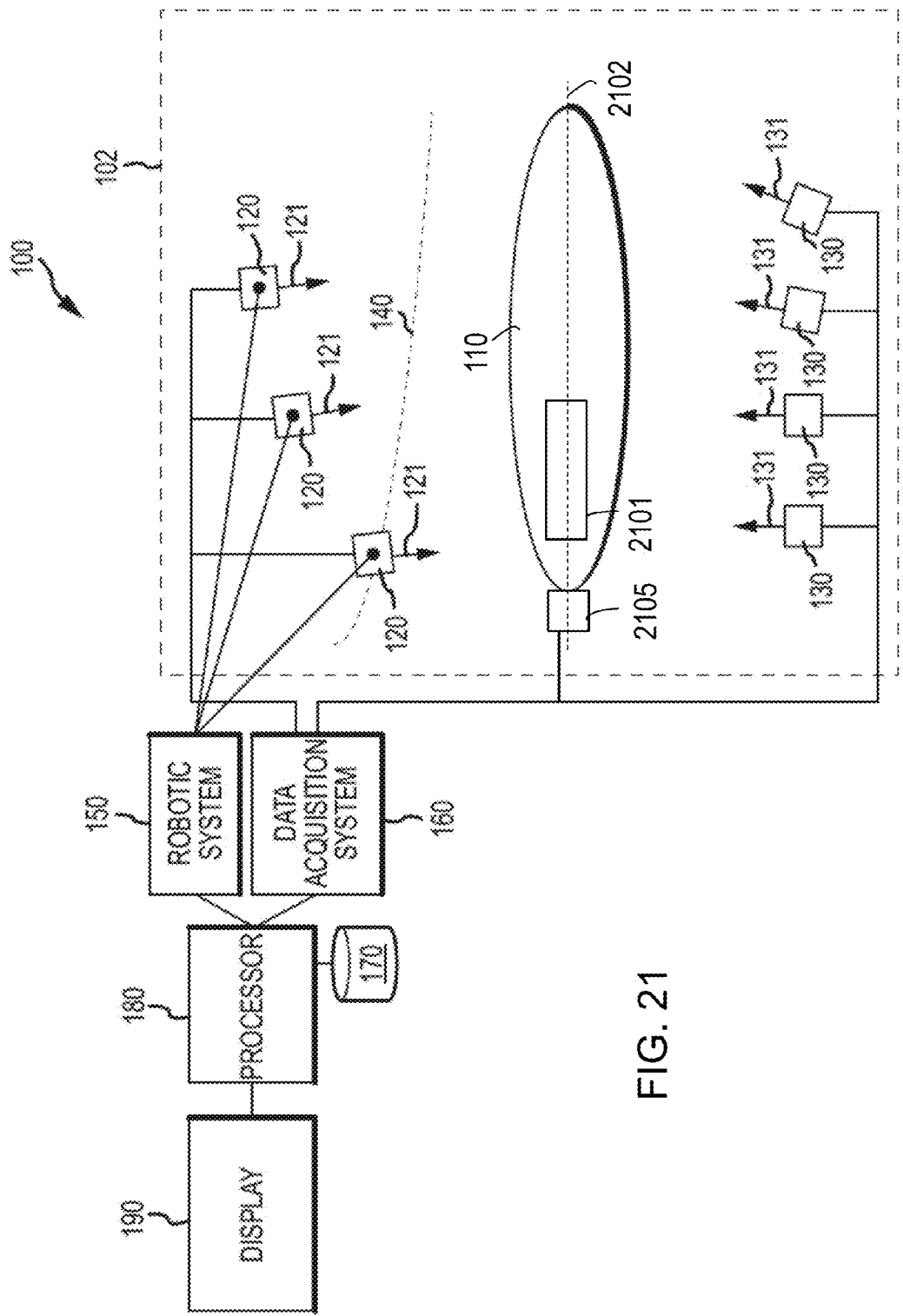
FIG. 21 is a conceptual block diagram of an imaging system in accordance with another embodiment of the invention.

FIG. 21 depicts a conceptual block diagram of an imaging system in accordance with another embodiment of the invention, in which the test subject 110 includes one or more rotational elements 2101—e.g., a shaft or other structure configured to rotate around an axis 2102 as shown. In this regard, the description that follows may, without a loss of generality, be described in the context of one or more rotating shafts. It will be appreciated that the invention is not so limited, however, and that the same methods may be applied to other rotating elements, such as fans, gearboxes, gear teeth, and turbo-pumps.

As shown in FIG. 21, imaging system 100 includes a rotational sensor 2105 configured to sense the rotational velocity as well as the angular position of element 2101 of test subject 110. Rotational sensor 2105 is suitably coupled to data acquisition system 160 through any convenient means of data or signal communication. In the interest of brevity, rotational sensor 2105 may be described as a "tachometer" herein, but may in fact comprise any suitable sensor capable of sensing rotational position. The remaining elements of FIG. 21 correspond to those of FIG. 1.

Figure 37:
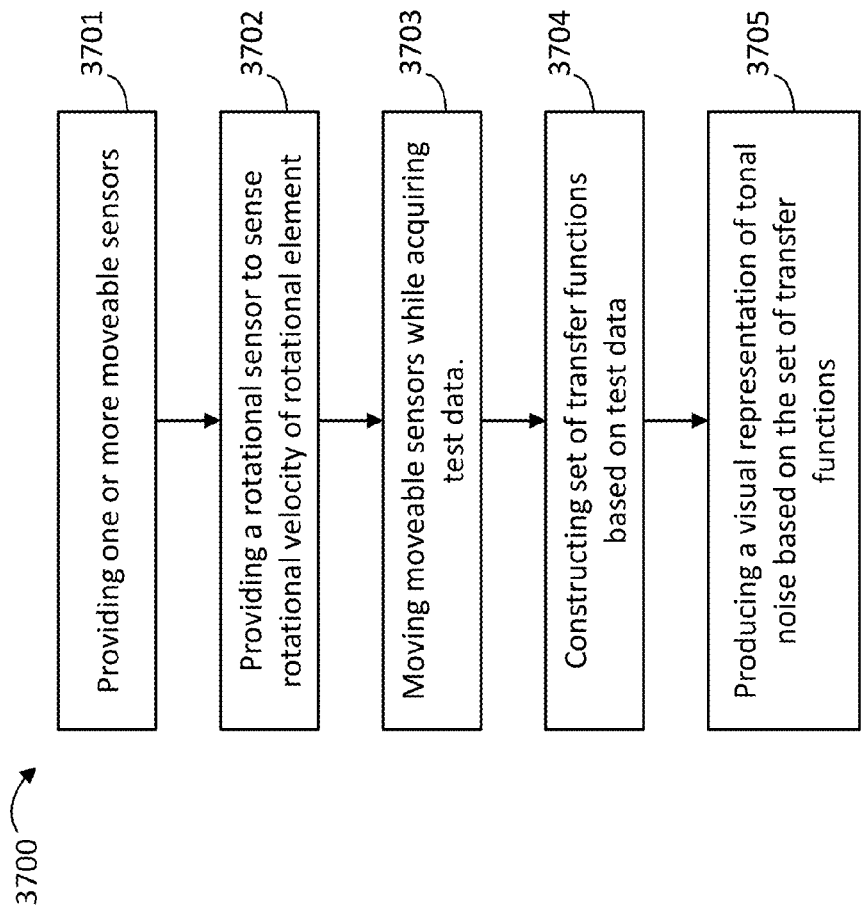
FIG. 37 is a flowchart depicting a method in accordance with one embodiment.

Having thus generally described an exemplary imaging system 100, a method of imaging a test subject will now be described in conjunction with the flowchart of FIG. 37 and the block diagram of FIG. 21. In general, the testing procedure generally includes providing one or more moveable sensors 120 as described above (step 3701). Moveable sensors are configured to sense an attribute of test subject 110 (e.g., acoustic noise), which has both a tonal noise component and a broadband noise component. Furthermore, a rotational sensor 2105 is provided within the test environment to directly (e.g., through a mechanical connection) or indirectly sense the rotational velocity of rotational element 2101 (step 3702). Next, in step 3703, each of the moveable sensors 120 are moved along a path while continuously acquiring test data that is indicative of the sensed attribute, the position and the orientation of each of the moveable sensors, and the rotational velocity of the rotational element 2101 (step 3703). A set of transfer functions are then constructed (step 3074) such that they correspond to points in space that the moveable sensors 120 have visited. Each of the transfer functions relates the test data of the moveable sensors to the test data of the rotational sensor. In a particular embodiment, constructing the transfer functions includes applying a Vold-Kalman Order Tracking Filter to extract time histories of tones that are coherent with orders or multiples of the fundamental shaft rotation frequency as sensed by rotational sensor 2105. Finally, a visual representation (e.g., a 3D or 2D plot) of the tonal noise component (i.e., the noise produced exclusively by rotational element 2101) using the set of transfer functions (step 3705).

In accordance with various embodiments, the above result may be accomplished in via three distinct steps: 1) Vold-Kalman filtering, 2) fractional-octave analysis, and 3) acoustic holography projection. Each of these steps will now be described in turn in the context of specific, but non-limiting, examples.

The Vold-Kalman Filter

The Vold-Kalman filter for time domain order tracking provides a number of unique capabilities, such as beat-free extraction of crossing orders; however, it has a gained a reputation as a technique requiring significant computational resources. The following description presents a new sequencing of equations, such that even in multiple shaft test cases (e.g., multiple rotational elements 2101) the resulting banded equations may be solved efficiently by direct methods, such as the banded Cholesky decomposition, as described in further detail below.

Non-stationary stochastic processes with finite second order moments may be decomposed into a sum of a purely deterministic process and a purely indeterministic process. This decomposition is customarily called the Wold decomposition and may be characterized as follows: purely deterministic means a process locally composed of sine waves with random frequency, amplitude, and phase. In mechanical systems, these are typically caused by rotating and reciprocating machinery. In contrast, purely indeterministic means a causal infinite length moving average driven by a white noise process. Causes of such noise include, for example, turbulence, vortex shedding and discrete event processes. It should be noted that, for example, narrow band aerodynamic effects are still purely indeterministic even though they may be visually indistinguishable from slowly varying sinusoids. These processes possess absolutely continuous spectra and are also known as broadband processes.

The Vold-Kalman filter is a practical algorithm for generating the Wold decomposition of a finite sampled, bandlimited process when the instantaneous state of the underlying periodic phenomena causing the purely deterministic component is known. The filter operates in the time domain, and uses a global estimation scheme, so there are no signal processing artifacts due to arbitrary block sizes and windows. The sinusoids are also estimated without phase bias because the formulation is symmetric in time.

Normally, the imaging system 100 will contain a sensor (e.g., sensor 2105 in FIG. 21), such as a tachometer or an encoder, for each independent locally periodic source in the system, which will serve as a phase reference for the harmonics, or orders that these sources generate.

A significant benefit of the time domain formulation is that the sinusoids will be known with both amplitude and phase as functions of time, and also that they will be mutually phase coherent with the causative shaft in a multi-channel situation. This allows the system to reconstruct the self-coherent spatial field corresponding to each order, limited only to the spatial distribution of sensors. When the signal sources are stationary, the coherence relative to the shaft associated with an order permits one to use continuously traversing arrays of sensors for the purpose of achieving higher spatial sampling densities.

A time domain separation into harmonics and broadband noise also allows for the usage of specialized analysis tools for each signal category, such as sideband demodulation for orders and fractional octave analyses for broadband signal components. The decomposition into a signal's various components is especially valuable in aeroacoustic and vibroacoustic applications, since the rotor harmonics and broadband flow noise may be analyzed separately.

Strictly speaking, the Vold-Kalman filter is a smoothing filter, not a real-time filter, as it requires information from the future and the past. Its computation requires the solution of a coupled linear system of equations, and, the only known practical methods for solving large multi-shaft problems involved iterative solution schemes, such as preconditioned conjugate gradients, with unpredictable accuracy and solution times. This deficiency has been noted with tracking the individual contributions from two independently running shafts in a dual rotor system. To be able to run the large number of large dual shaft filtering problems for hundreds of orders, the present inventor devised a sequencing scheme for the sparse equations that resulted in a huge, but manageable coefficient matrix with a small bandwidth, such that solutions could be obtained in a reasonable amount of time on ordinary desktop computers.

Another complicating factor of the Vold-Kalman filter is that the numerical ill-conditioning of the coefficient matrix associated with the computation of the filter becomes severe when the filter passband width is narrowed, ultimately resulting in nonsense results. Again, this has been found to be a concern with dual rotor projects. In accordance with the present invention, a solution was found in a square root formulation of the filter, using unitary Householder reflections. It was implemented using a "QR" algorithm, and it successfully allowed for much tighter passbands to be used, albeit at the cost of doubling the computation time.

A short mathematical background of the methods described herein will now be set forth. Herman Wold, a Norwegian-Swedish mathematician, formulated the first versions of what would become known as the Wold decomposition of any stationary stochastic process into the uncorrelated sum of a purely deterministic process and a purely indeterministic process. The deterministic process could be regarded as a sum of sine waves with various phases and amplitudes, and the purely indeterministic component could be represented as a white noise process filtered by an (infinite) moving average filter.

The sine waves would have point spectra with finite spectral mass at discrete frequencies, while the purely indeterministic component would have an absolutely continuous spectral density, corresponding to a broadband noise process.

As mentioned above, in rotating and reciprocating machinery there exists one or more rotating shafts which may be coupled mechanically through gears, belt and chains, or, electronically through feedback control systems. The rotations of these shafts will cause periodic vibrations, modulated by gears meshing, belts driving pulleys, cams operating valve trains and axial and thrust bearings supporting shafts, pulleys and gears. The periods of these vibrations will be purely kinematic functions of the mechanical layout of the machinery. The combustion or pressure cycles of such machines will also produce periodic excitation.

Let us denote the instantaneous speed of a shaft in revolutions per second as $\omega(t)$. The instantaneous rotational displacement is the time integral of the speed, and define the complex phasor $p_k(t)$ belonging to the order k as:

$$p_k(t) = \exp(2\pi i k \int_0^t \omega(u) du) \qquad (27)$$

The order k does not have to be an integer; toothed gears give rise to rational orders, and rolling element bearings and pulleys most often produce irrational orders.

One can now define a complex order time history $x_k(t)$ as $$x_k(t) = A_k(t) p_k(t) = A_k(t) \exp(2\pi i k \int_0^t \omega(u) du), \qquad (28)$$

where $A_k(t)$ is a slowly varying complex envelope.

This allows one to express the general case of a vibration or acoustic time history resulting from the periodic components of a rotating or reciprocating machine as $$x(t) = \sum_{s \in S} \sum_{k \in K_s} A_{sk}(t) p_{sk}(t) \qquad (29)$$

$$= \sum_{s \in S} \sum_{k \in K_s} A_{sk}(t) \exp\left(2\pi i k \int_0^t \omega_s(u) du\right),$$

where S is the set of all independently moving shafts, and $K_S$ is the set of all orders, negative as well as positive, generated by shafts.

Since equation 29 is a sum of sine waves, this time history is a completely deterministic process in the language of the Wold decomposition. Because of this property, each order, when observed synchronously with multiple sensors is fully self coherent, which makes is feasible to construct spatial mappings of each order as a function of time, rpm or frequency.

In the real world, when one measures the structural and acoustic responses from rotating and reciprocating machinery, one will also record the effects of flow noise, turbulence and transient events, in addition to the sum of periodic signals x(t) from equation 29, such that the total measured signal y(t) will be of the form:

$$y(t) = x(t) + v(t), \qquad (30)$$

where v(t) is causal, is uncorrelated with x(t), and has an absolutely continuous spectrum without point masses. The broadband signal v(t) is thereby the purely indeterministic component of the Wold decomposition.

It will now be assumed that we have digitized a finite alias free response time history y(n); $n \in [0, 1, \ldots, N]$ where the sampling rate has been set to one sample per second without loss of generality. We also assume that we have obtained the shaft speeds $\omega_s(n)$ for the shafts by observing encoders or tachometers. Order tracking includes estimating the complex envelopes $A_{sk}(n)$ from the recorded response and shaft speeds for the orders $k \in K_s$, restricted to the orders less in frequency than the Nyquist frequency 0.5 Hz. The Vold-Kalman filter is related to the classical Kalman filter by compromising between structural equations and data equations, although in the Vold-Kalman filter one only uses the ratio between the two sets of equations.

The structural equation specifies that the envelope functions should be smooth, slowly varying functions. One way of specifying this for the envelope $A_{sk}(n)$, is to demand that a repeated difference should be small, e.g., satisfy one of the following equations (eq. 31-33):

$$\nabla A_{sk}(n) = A_{sk}(n+1) - A_{sk}(n) = \epsilon(n),$$

$$\nabla^2 A_{sk}(n) = A_{sk}(n+2) - 2A_{sk}(n+1) + A_{sk}(n) = \epsilon(n),$$

$$\nabla^3 A_{sk}(n) = A_{sk}(n+3) - 3A_{sk}(n+2) + 3A_{sk}(n+1) - A_{sk}(n) = \epsilon(n),$$

where the sequence $\epsilon(n)$ is small in some sense. The exponent q in the difference operator $\nabla^q$ is customarily named the pole count of the Vold-Kalman filter. The coefficients of the expanded iterated differences are seen to build the famous Pascal triangle. In addition to the smoothness condition of the structural equation, the estimated complex envelope function must somehow be related to the measured data, and this is achieved by the data equation $$\sum_{s \in S} \sum_{k \in K_s} A_{sk}(n) p_{sk}(n) - y(n) = v(n), \qquad (34)$$

which is seen to be a reordered discrete version of equations 29 and 30. It can be seen that the unknown complex envelope functions $A_{sk}(n)$ occur in linear expressions with measured coefficients on the left hand side of the structural and data equations, so we can construct a weighted linear least squares problem by choosing a weighting function r(n), $n \in [0, 1, \ldots, N]$, and discarding the unmeasured functions $\epsilon(n)$ and v(n) as nuisance parameters to obtained the linear, overdetermined set of equations (35, 36):

$$r(n) \Delta^q A_{sk}(n) \approx 0$$

$$\sum_{s \in S} \sum_{k \in K_s} A_{sk}(n) p_{sk}(n) \approx y(n),$$

where a large value of r(n) enforces smoothness around the time point n, while a small value permits the observed data to dominate the estimation at this time point. It will be seen that the choice of the weighting function r(n) determines the bandwidth and the resolution of the results.

A minimum bandwidth ordering of the equations associated with the least squares solution of the overdetermined equations 35 and 36 can be determined by defining a total ordering on the set of unknown complex envelopes $$A_{sk}(n) \text{ for } s \in S, k \in K_s \text{ and } n \in [0,1, \ldots, N] \qquad (37)$$

Defining an arbitrary ordering on the set of shafts S and using the usual ordering on the orders and the discrete time points, the corresponding lexicographical ordering then works as (eq. 38):

$$[s', k', n'] < [s, k, n] \Longleftrightarrow \begin{cases} n' < n, \\ \text{or } n' = n \text{ and } s' < s, \\ \text{or } n' = n \text{ and } s' = s \text{ and } k' < k. \end{cases}$$

By inspection of equations 35 and 36, one can easily determine that two unknowns $A_{s'k'}(n')$ are coupled only if the difference in the absolute value of n'−n is less than or equal to q, where q is the pole count for the filter.

If the total number of orders is denoted $N_o$, the computational complexity of any least squares solution with this ordering is proportional to $(qN_o)^2$ and linear with N, the length of the digitized time series.

It is assumed herein that the asymptotic properties of the weighting function r(n) are determined by investigating a simplified version of equations 35 and 36, whereby we use a constant positive real value of r, and a single order with zero shaft speed and an observed response time history which is a stationary phasor with frequency $\omega$ (eq. 39, 40):

$$r\nabla^q A(n) \approx 0.$$

$$1 A(n) \approx \exp(2\pi i n \omega).$$

The least squares steady state solution must be a complex multiple of the phasor, say $\tilde{A} \exp(2\pi i \omega - 1) - 1)$ and so, one has the relation:

$$(r^2(\exp(2\pi i \omega)-1)^q(\exp(-2\pi i \omega)^q-1)+1)\tilde{A}=1, \quad (41)$$

or, rearranged, $$\tilde{A} = (1+r^2(2-2\cos(2\pi\omega))^q)^{-1} \quad (42)$$

The amplitude of $\tilde{A}$ as a function of frequency represents the selectivity of the filter away from the center frequency, and may be regarded as the transfer function of the filter.

Figure 22:
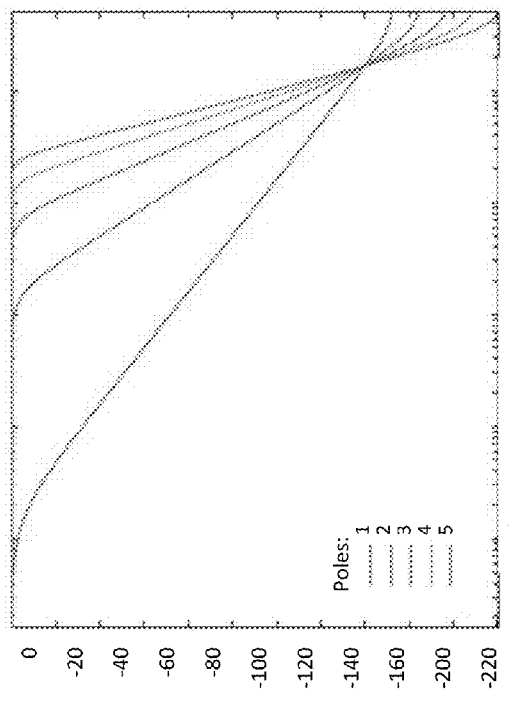
FIGS. 22 and 23 are graph showing example filter response characteristics plotted against pole count.

Note that the phase is zero, so this filter has no phase bias. The transfer function is plotted in FIG. 22 as a function of frequency for various values of the difference operator and the weighting r set to $10^4$. In order to choose the weighting which gives a 3 dB roll-off at a selected bandwidth, we use equation 42, let $\tilde{A}=1/\mathrm{sqr}(2)$ and solve for r, giving $$r = \sqrt{\frac{\sqrt{2}-1}{(2(1-\cos(2\pi\omega))^q}} . \quad (43)$$

Figure 23:
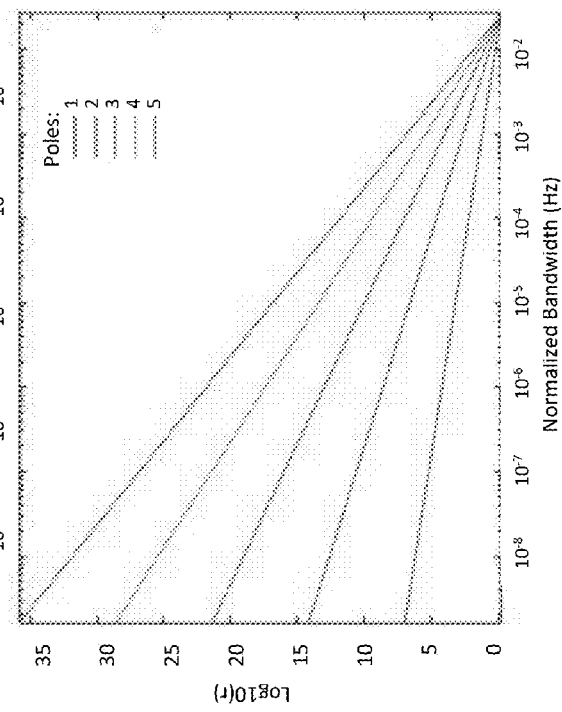
Figure 24:
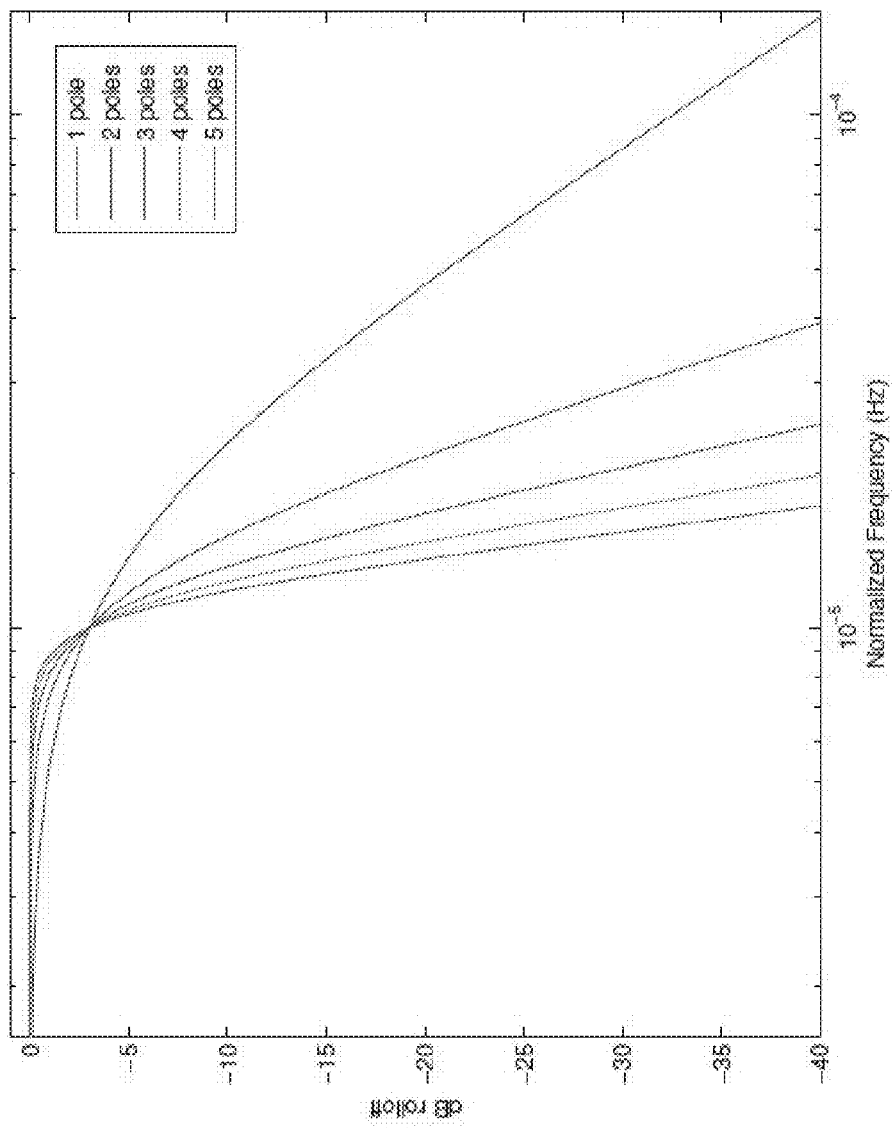
FIG. 24 is a graph showing example filter transfer functions for various pole counts.

The weighting factor is plotted logarithmically in FIG. 23, whereby it is seen that its dynamic range quickly exceeds the mantissa of approximately 16 decimal digits in IEEE double precision floating point. Some of the consequences of this excessive dynamic range will be investigated more in detail in the section on the least squares QR solution scheme. By plotting the transfer functions of the Vold-Kalman filter for a fixed bandwidth selection and the lowest pole counts, FIG. 24, it can be seen that the filters are monotone and that the filter selectivity improves with increasing pole count. By inspection of the structural equation 35, we see that there is a totality of $N_o(N+1)$ scalar difference equations, so it is possible, and often desirable, to apply a separate weighting function r for each order, for example to enforce a frequency proportional bandwidth to each order when the shaft speeds have a high dynamic range.

Using the lexicographical ordering, the overdetermined equations 35 and 36 may be written in matrix form as $$\left\{\begin{array}{c} R\Delta \\ P \end{array}\right\} A \approx \left[\begin{array}{c} 0 \\ y \end{array}\right], \quad (44)$$

where R is the diagonal matrix formed by the elements of the weighting coefficients $r_{sk}(n)$ in lexicographical order, A is the banded matrix of the iterated difference coefficients, P is a banded matrix of the complex phasors $p_{sk}(n)$), and A is the column vector of the complex envelopes $A_{sk}(n)$ in lexicographical order.

The usual least squares solution by normal equations is found by premultiplying equation (44) by the conjugate transpose of the coefficient matrix and using the Cholesky decomposition to solve the banded hermitian set of equations $$(\Delta^H R^2 \Delta + P^H P) A = P^H y \quad (45)$$

Inspection of this equation highlights the problem that the large values in R, see, e.g. FIG. 23, are squared up and then get added to the phasor values in P, which are complex numbers on the unit circle. When the r values are of the order of $10^8$ and larger, the mantissae of the phasor values get lost in IEEE double precision floating point arithmetic, and equation 45 becomes numerically singular. There is hence a practical lower limit for the attainable bandwidth of the Vold-Kalman filter when the classical normal equations technique is applied.

We may instead apply the QR method, a sequence of unitary Householder reflections $Q_1 Q_2 \ldots = Q_M = Q$ that transforms the coefficient matrix of equation 44 into an upper triangular matrix. This sequence may be constructed to preserve the bandedness of the equations, and gives the equivalent equation $$Q\left\{\begin{array}{c} R\Delta \\ P \end{array}\right\} A = \left\{\begin{array}{c} U \\ 0 \end{array}\right\} A \approx Q\left[\begin{array}{c} 0 \\ y \end{array}\right] = \left[\begin{array}{c} \hat{y} \\ \hat{\epsilon} \end{array}\right], \quad (46)$$

where U is an upper triangular matrix and Q is a unitary matrix. Unitary matrices represent isometries, i.e., for all vectors y, $\|Q_y\|=\|y\|$, so that they do not cause distortion, only reorientation. One can now solve equation 44 by backward substitution as $A=U^{-1}\hat{y}$.

In this formulation, the large weighting values in R have not been squared up, but only reflections and rotations have been applied, so the values in R may grow to $10^{15}$ before the IEEE double precision significance cancellation occurs, and hence the bandwidth specifications may be tightened up. The downside of the QR method is that the number of arithmetic operations is roughly twice that of the normal equations with Cholesky decomposition.

A substantial reduction in computation and storage is possible for the important case of a single shaft with the same bandwidth specification for all the orders. Consider a single order k to be extracted with a corresponding weighting function r(n) and the phasor:

$$p_k(n) = \exp(2\pi i k \Sigma_{l=0}^n \omega(l)) \quad (47)$$

The overdetermined equations 35 and 36 simplify to (eq. 48, 49):

$$r(n) \nabla^q A_k(n) \approx 0$$

$$p_k(n) A_k(n) \approx y(n),$$

where equation 49 may be rewritten as $$1 A_k(n) \approx p_k^{-1}(n) y(n), \quad (50)$$

whereby it is seen that the left hand side becomes that of a phasor of constant frequency zero, and a time variant zoom transformation on the right hand side. The coefficient matrix is then of length N+1, and semi-bandwidth q+1. If we now denote the set of orders to be extracted as $[k_1, k_2; \ldots, k_K]$, the equations to be solved will have the single order independent left hand side, with K right hand sides of the form $p_{kj}^{-1}(n)y(n)$, for $k_j \in [k_1, k_2, \ldots, k_K]$. The inverses of the phasor functions may always be applied, since the absolute value of any phasor is always one.

In accordance with one example, it can be demonstrated how the QR decomposition method can be superior to the Cholesky decomposition for difficult order tracking problems. In this numerical example there are three shafts with orders and speed profiles as summarized in table 1, which shows the speeds and orders for a three shaft numerical example. Shaft #2 simulates an order with sideband modulation.

TABLE 1

| Shaft | Min Speed | Max Speed | Type | Direction | Orders |
|---|---|---|---|---|---|
| 1 | 500 | 1000 | Linear | Descending | [0.8, 1.0, 1.3, 1.5] |
| 2 | 500 | 1100 | Log | Ascending | [1.000, 1.0002, 1.0004, 1.0006] |
| 3 | 500 | 550 | Const. | | [1.0, 1.24, 1.47, 1.71, 1.94, 2.18] |

Figure 25:
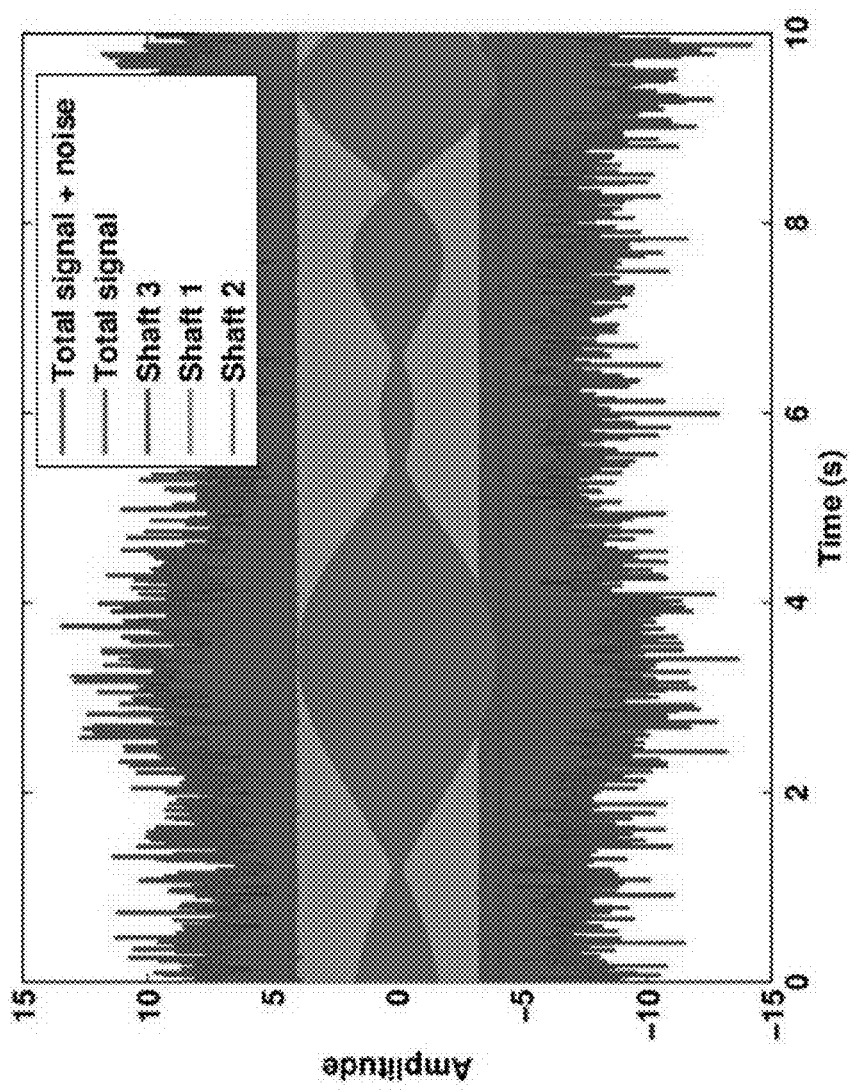
FIG. 25 is a graph depicting Wold decomposition of a synthetic noisy signal.
Figure 26:
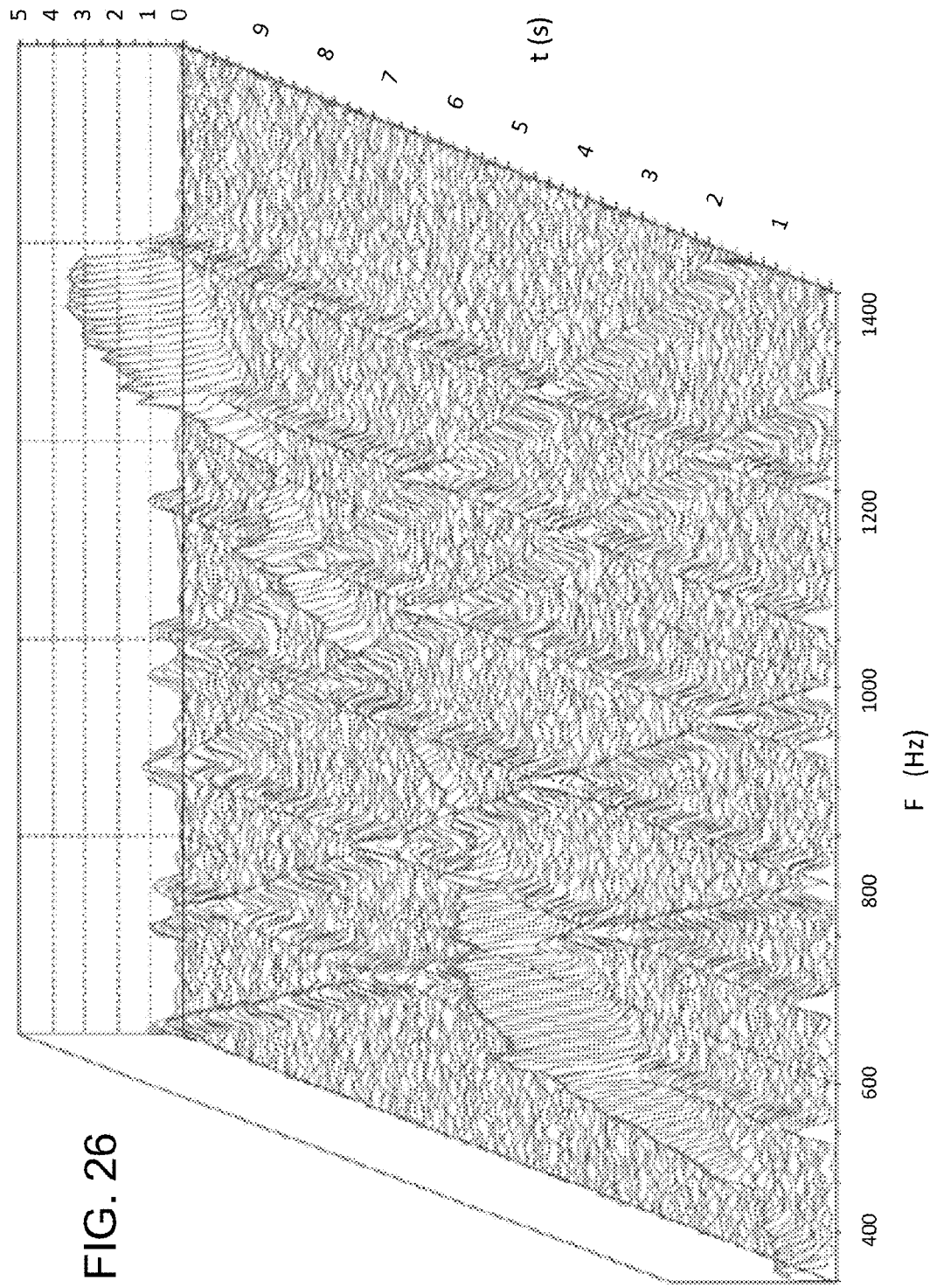
FIG. 26 is a waterfall plot of frequency vs. elapsed time in accordance with one example.

All orders have a constant amplitude of one, but with a random phase lag. The orders for shaft #2 simulate a sideband condition, with four orders separated by 0.0002 of an order. The constant frequency orders could represent electrical network noise. The experiments lasted ten seconds, and the data was sampled with a sampling frequency of 8,192 Hz. The individual orders were first accumulated per shaft, then summed into a single time history of sinusoids, and finally, Gaussian noise with a standard deviation of 2.0, was added in to represent the purely indeterministic component of the signal. FIG. 25 shows an overlay of the signals with the order time histories belonging to each of the three shafts. The plot shows how the dense sidebands of shaft #2 generate a non periodic beating over the observation window. The waterfall of frequency versus time for the total signal is shown in FIG. 26.

Figure 27:
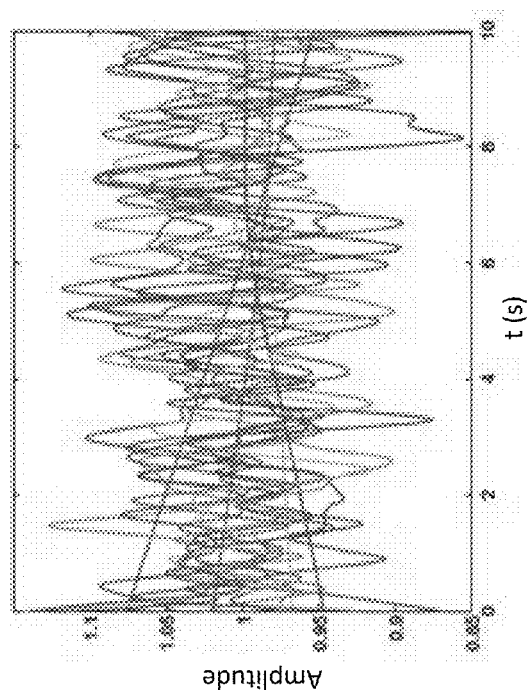
FIGS. 27 and 28 are graphs depicting example amplitudes of all orders estimated in accordance with a bandwidth of 0.01% of an order.
Figure 28:
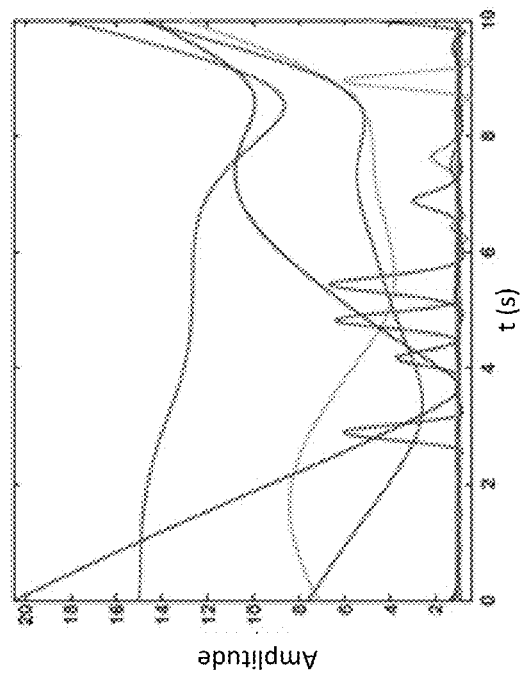
Figure 29:
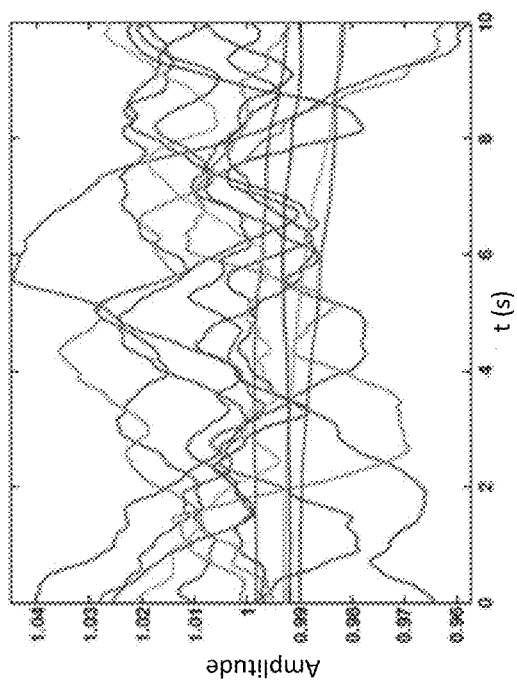
FIGS. 29 and 30 are graphs depicting example amplitudes of all orders estimated in accordance with a bandwidth of 0.001% of an order.
Figure 30:
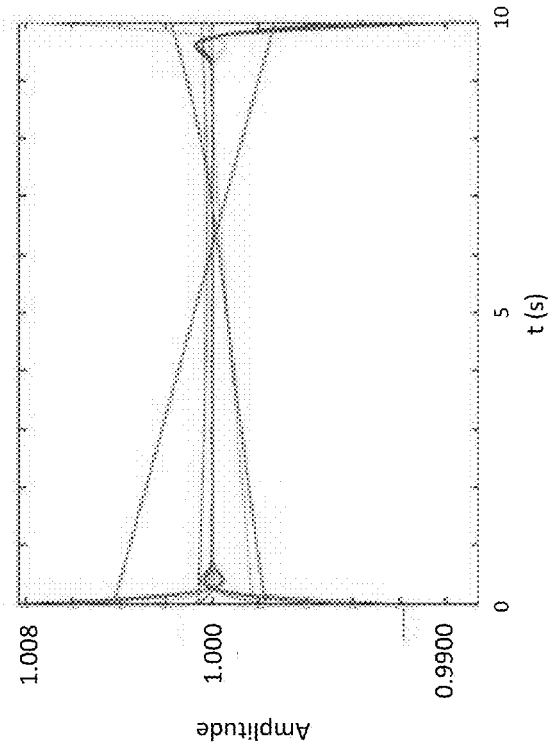

It is now desired to extract the all the present orders from the noisy summed signal, and for the orders generated by shaft #2 one must specify a bandwidth of no larger than 0.01% of an order. The least squares equations are formed and solved with both the QR and the classical Cholesky algorithm in IEEE double precision floating point arithmetic. The resulting estimated order amplitudes are shown in FIGS. 27 and 28, in which each order amplitude is represented by a different color, and the smooth curves belong to shaft #s. It is evident that the QR results (FIG. 27) are reasonable, whereas the Cholesky algorithm (FIG. 28) fails due to numerical error. Inspection of FIG. 27 further indicates that in spite of the narrow bandpass filter, the background noise still contaminates the order estimates by approximately 10% relative error. As a final check, the filter bandwidth can be tightened to 0.001% and the QR algorithm applied to both the noisy and the clean signal. FIG. 29 illustrates the QR decomposition estimates (each associated with a different color) with 4% relative error. The smooth curves belong to shaft #2. FIG. 29 thus shows that the relative error reduces down to approximately 4% for the noisy signal, whereas the error in the clean signal, as shown in FIG. 30, is miniscule.

Figure 31:
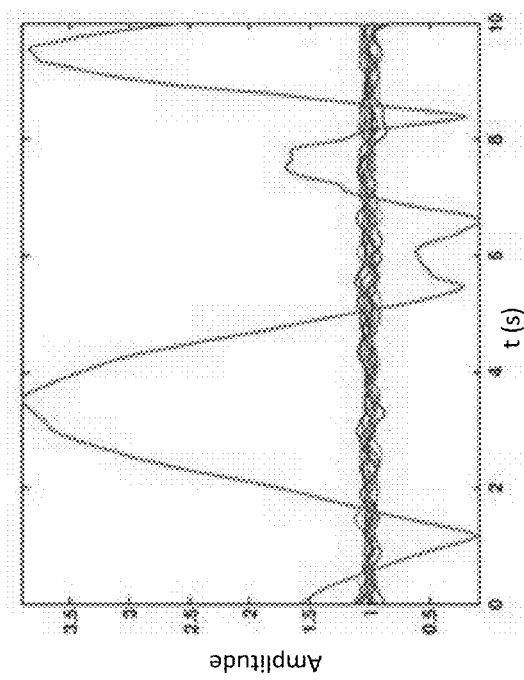
FIGS. 31 and 32 are graphs depicting example amplitudes of all orders estimated in accordance with a bandwidth of 1% of an order.
Figure 32:
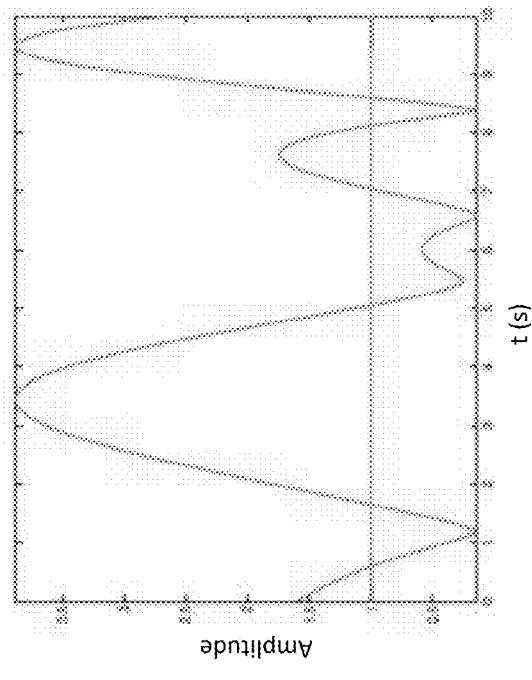

The densely clustered orders of shaft #2 can be extracted as a single entity by widening the bandwidth to 1% of an order. One can filter both the clean and the noisy signal and find that both the QR and Cholesky algorithms give the same results with this wider bandwidth setting. FIG. 31 shows that the well separated orders are still estimated with their unit amplitude, while the sidebands from shaft #2 are now collected into the envelope of the beating signal. Furthermore, comparison of FIGS. 31 (noisy) and 32 (clean) shows that the broadband Gaussian noise still contaminates the filtered bands to some extent.

The following example deals with a dual-rotor propulsion unit in wind tunnel, in which the test subject consists of two counter rotating spools with a non-rotating center shaft. Each of the two counter rotating spools is attached to a two-stage air turbine on the aft end that can produce up to 560 kW (750 HP). While the speed of the rig is controlled by a feedback controller, the rotation rate of the two rotors (determined via a rotational sensor, as discussed above) varies slightly, and the phase is not locked between the rotors. This makes the two rotors behave slightly incoherently, and therefore, each rotor has its own discernible signature, which allows the Vold-Kalman filter to extract the individual contribution of the rotors.

Figure 33:
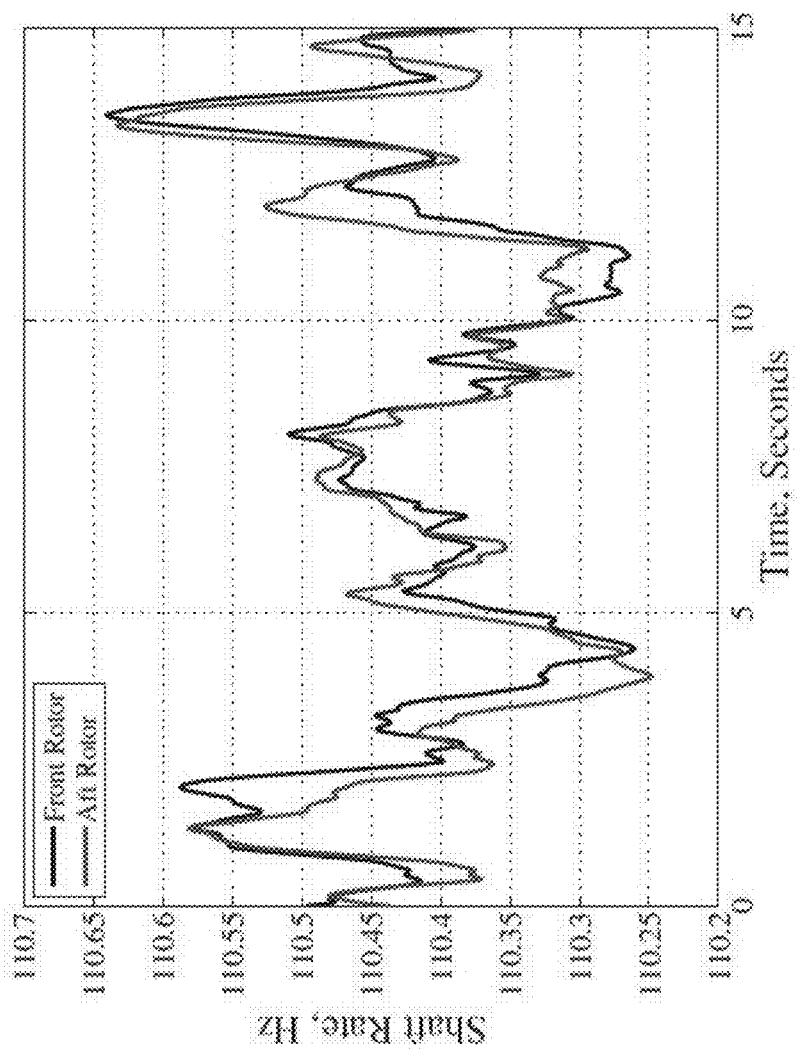
FIG. 33 is a graph depicting sample rotation speed traces in accordance with one example.
Figure 34:
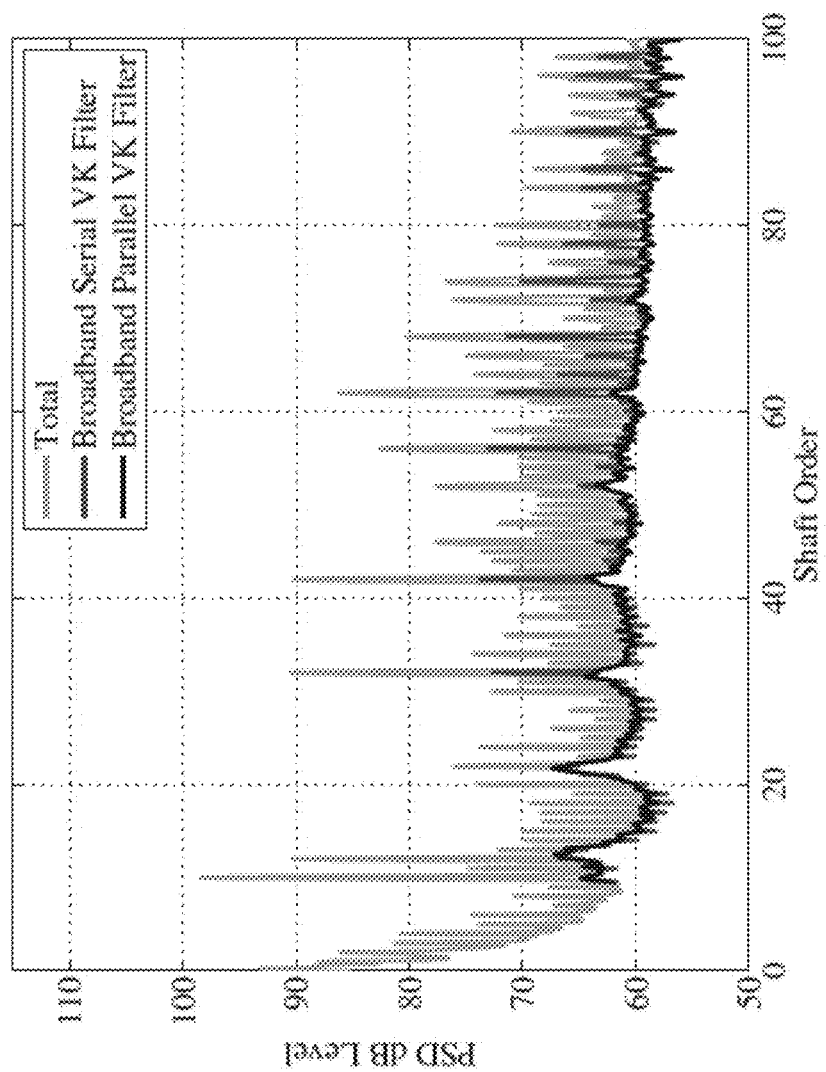
FIG. 34 is a graph depicting the comparison of serial and parallel Vold-Kalman filter processing.
Figure 35:
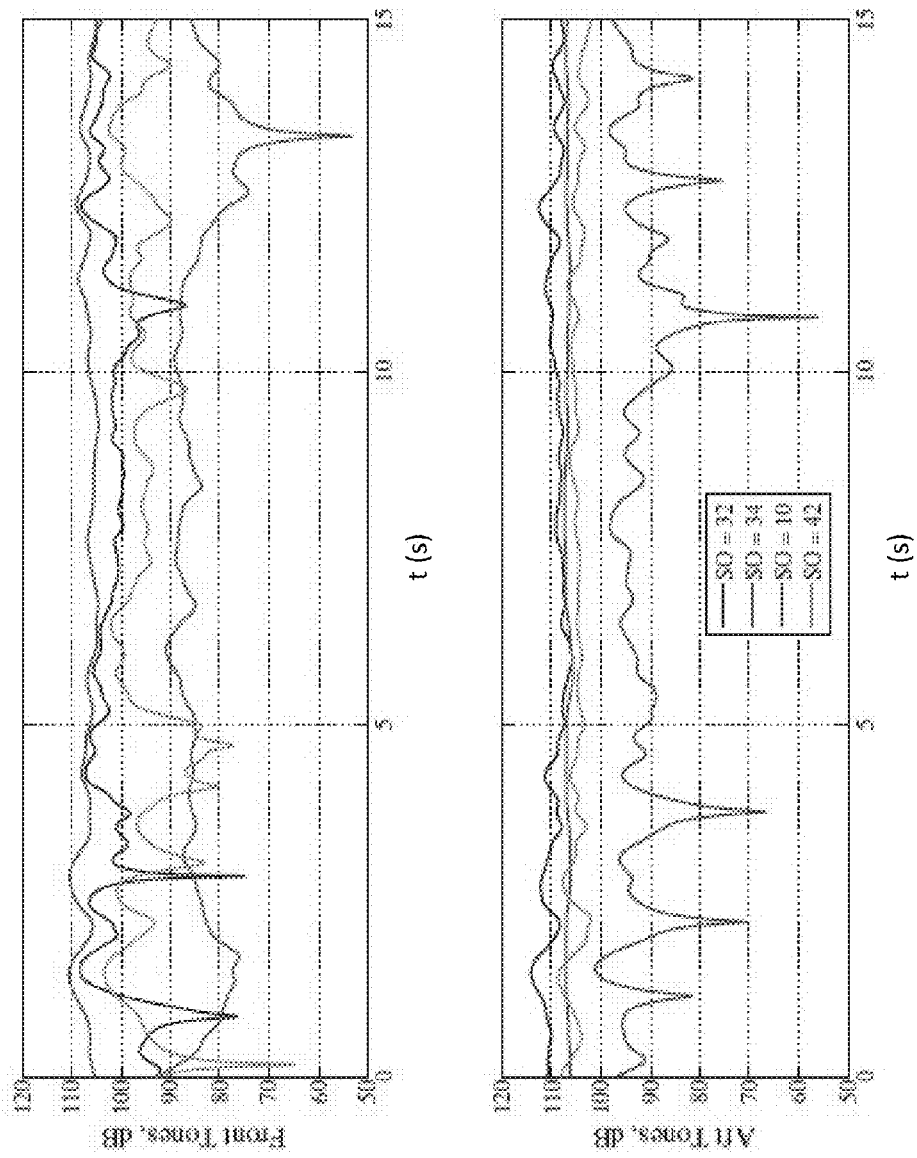
FIG. 35 is a graph depicting tone level fluctuations in accordance with one example.

A chart of the rotation speed measured for the two rotors is shown in FIG. 33. Microphone and tachometer data were analyzed at 100 KHz sampling rate, and orders 10 through 100 relative to each rotor were extracted as time histories. The front rotor had 12 blades, and the rear rotor had 10 blades. Two analyses were performed, the first by serially filtering the orders of each rotor individually, and the second by extracting the orders of the two rotors in parallel. In both cases, the extracted order time histories were subtracted from the total signal to estimate the broadband, purely indeterministic, component of the signal. FIG. 34 shows an overlay of the order spectra of the total signal, the broadband estimate from sequential order extraction and finally from the simultaneous extraction. The simultaneous extraction have substantially removed the bulk of the rotor harmonics, while the sequential processing has left significant harmonic residuals as well as visible divots in the broadband floor. Closer inspection reveals that the high harmonic residuals left by the one rotor at-a-time processing happen at the rotor interaction orders, namely orders of the form 12m+10n, where m and n are integers. For such orders, the multi-shaft application of the Vold-Kalman filter is a necessity. The independent behavior of the rotors allows for the estimation of the effects of each rotor separately. In the experiment, the four largest orders were selected, all of them interaction tones, with the exception of order 10, listed in Table 2 and plotted the amplitude for each order contribution from the front and the rear rotor as functions of elapsed time in FIG. 35.

TABLE 2

| Shaft Order (SO) | Front | Aft | Comment |
|---|---|---|---|
| 10 | 0 | 1 | single aft |
| 32 | 1 | 3 | multiple aft |
| 34 | 2 | 1 | multiple front |
| 42 | 1 | 4 | multiple aft |

Inspection of this figure shows reasonable behavior, e.g., that the energy from shaft order (SO) 10, which is the first bladepass of the rear rotor, is primarily emanating from this rotor. The energy from SO 34, which contains two bladepasses from the front rotor, and one from the rear is dominant in the front rotor, while SO 32 and 42, which contain multiple bladepasses from the rear rotor are dominated by the rear rotor contributions.

Figure 36:
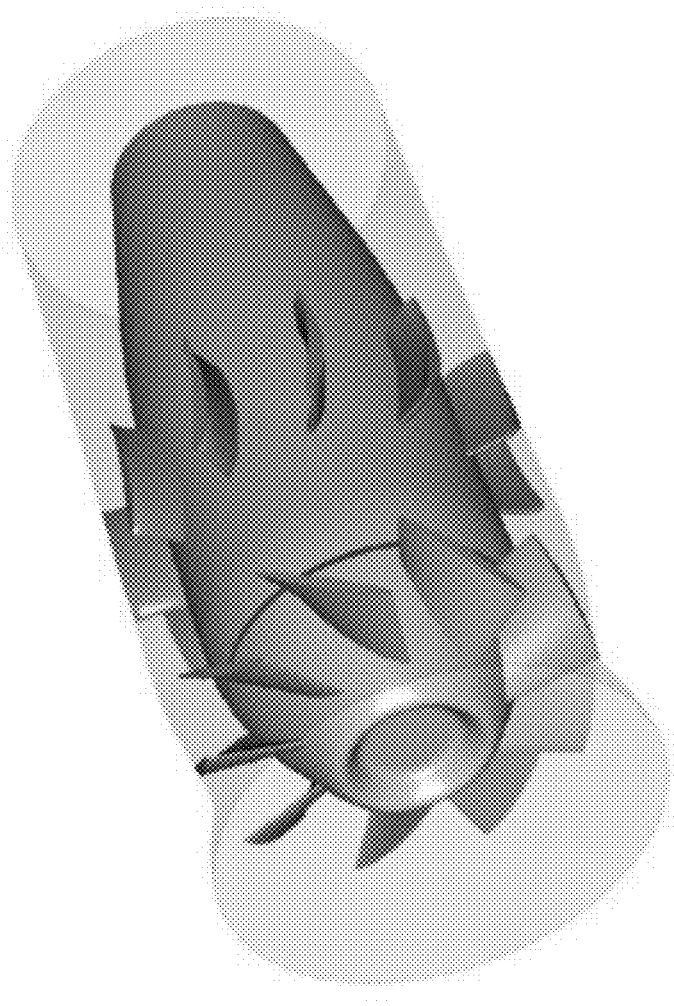
FIG. 36 is a transparency view of a ducted spacecraft ventilation fan in accordance with one example.

It will be appreciated that the foregoing examples are not intended to be limiting, and that the disclosed method may be employed in conjunction with any test object that includes one or more rotational elements, for example, a ducted axial fan as shown in FIG. 36.

Fractional-Octave Analysis of Time-Domain Separated Broadband, Harmonic, and Total Signals The foregoing section provided a detailed analysis of Vold-Kalman filtering as it may applied in various contexts. What follows is a detailed description of fractional-octave analysis of the resulting separated signals produced in a similar context from measurements of a scaled turbofan. For additional technical details regarding test conditions and the like, see Parthiv N. Shah, Håvard Vold, Dan Hensley, Edmane Envia, and David Stephens, *A High Resolution, Continuous-Scan Acoustic Measurement Method for Turbofan Engine Applications*, Proceedings of the ASME Turbo Expo 2014, GT-2014-27108 (2014).

Figure 38:
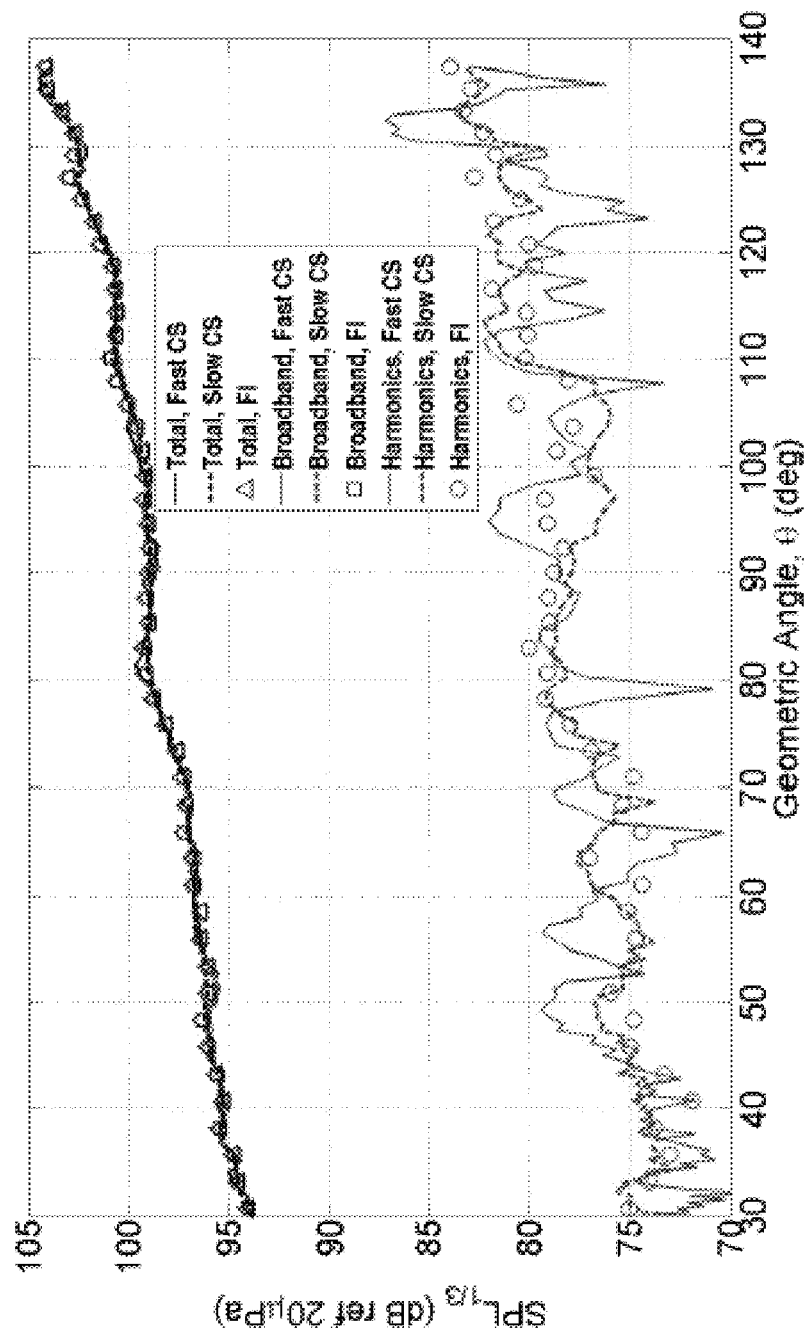
FIGS. 38-40 are graphs depicting one-third-octave directivities in accordance with various examples.
Figure 39:
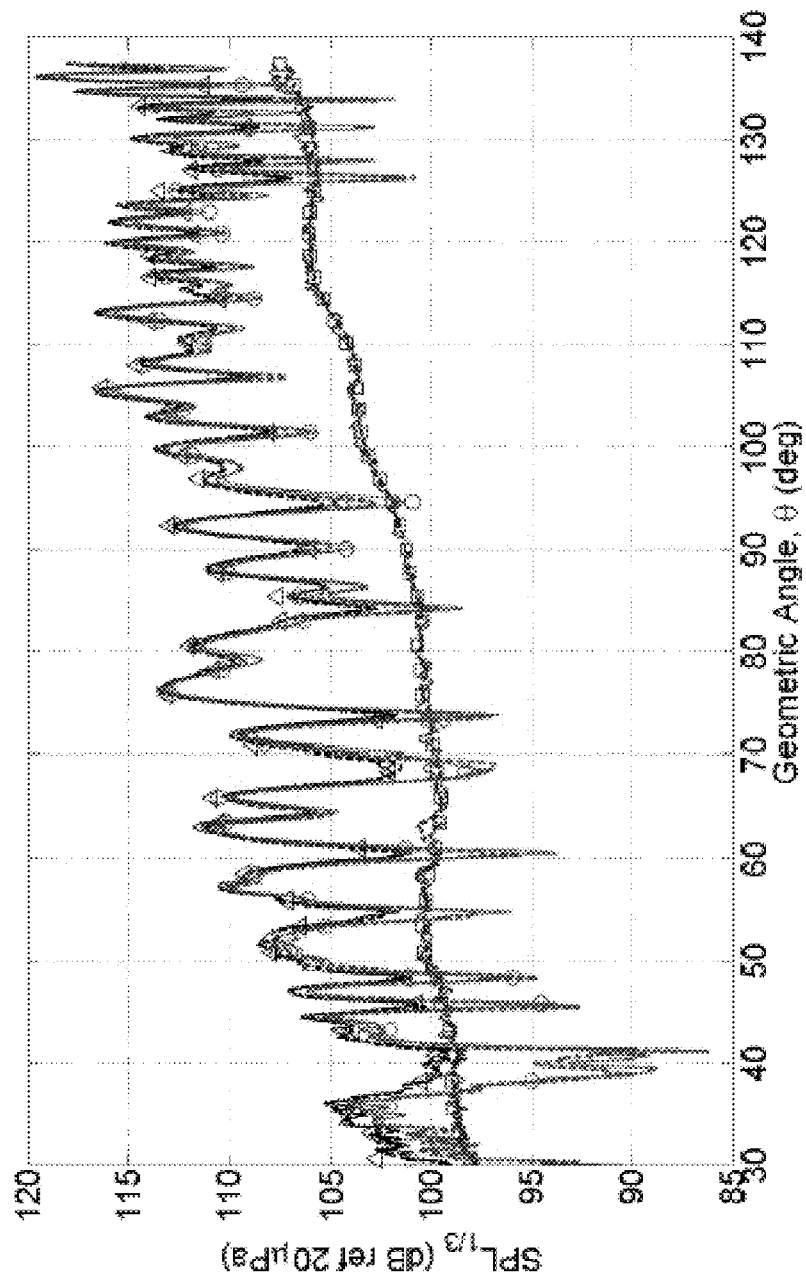
Figure 40:
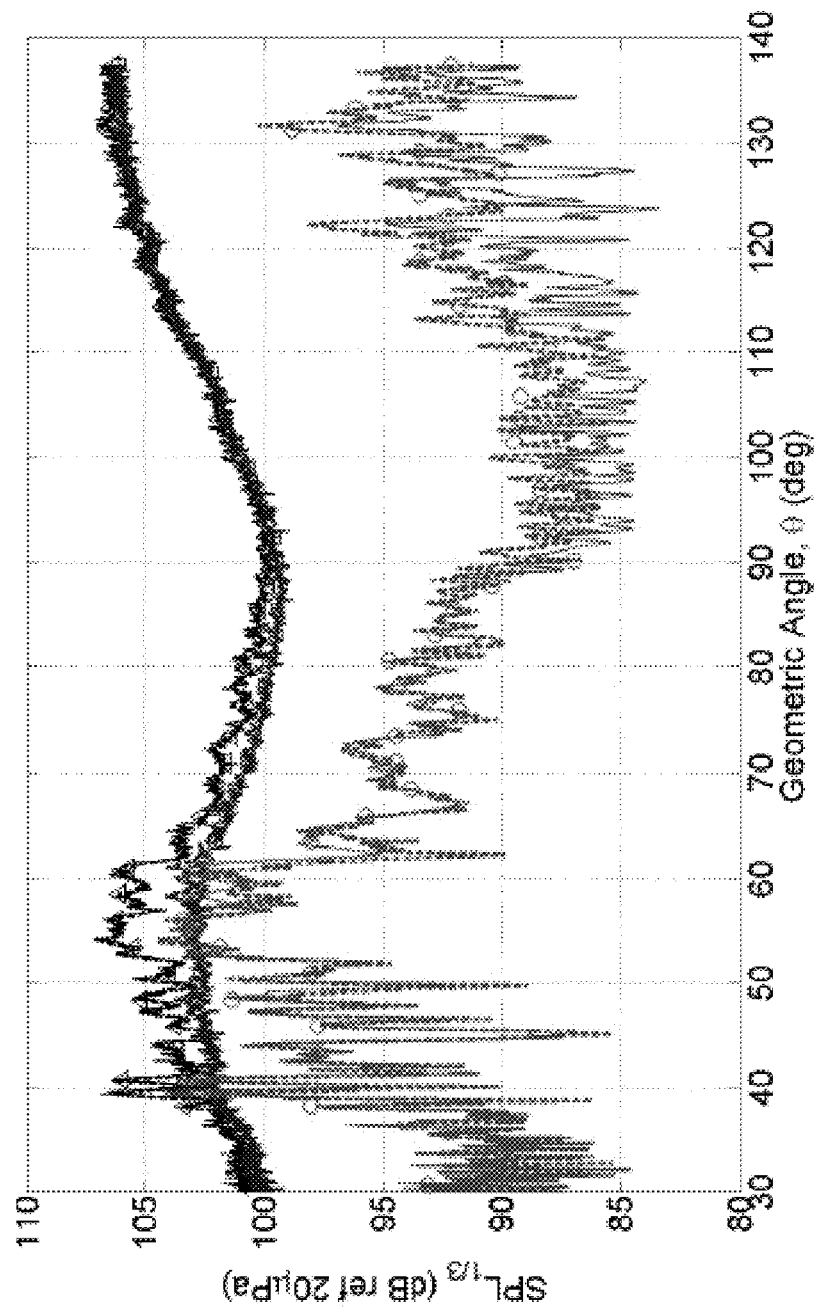
Figure 41:
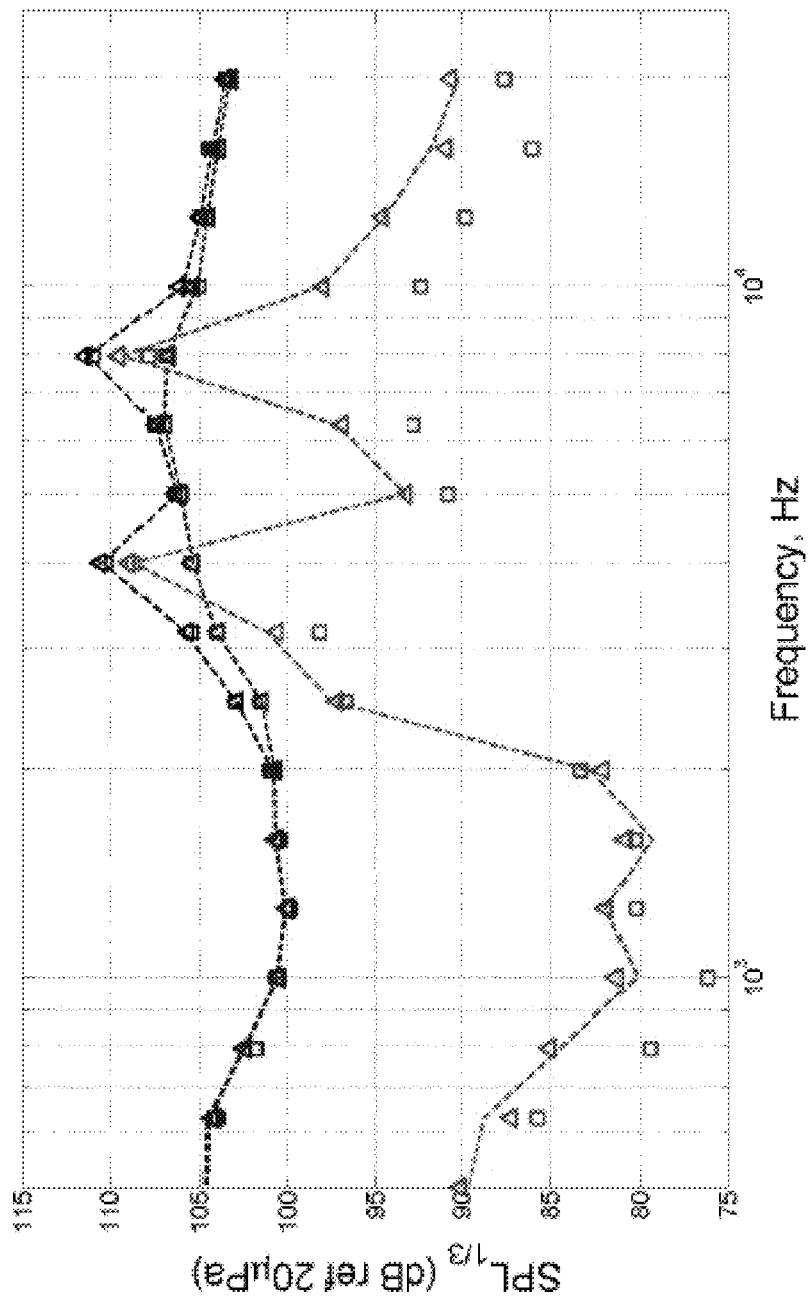
FIGS. 41-42 are graphs depicting one-third-octave spectra in accordance with various examples.
Figure 42:
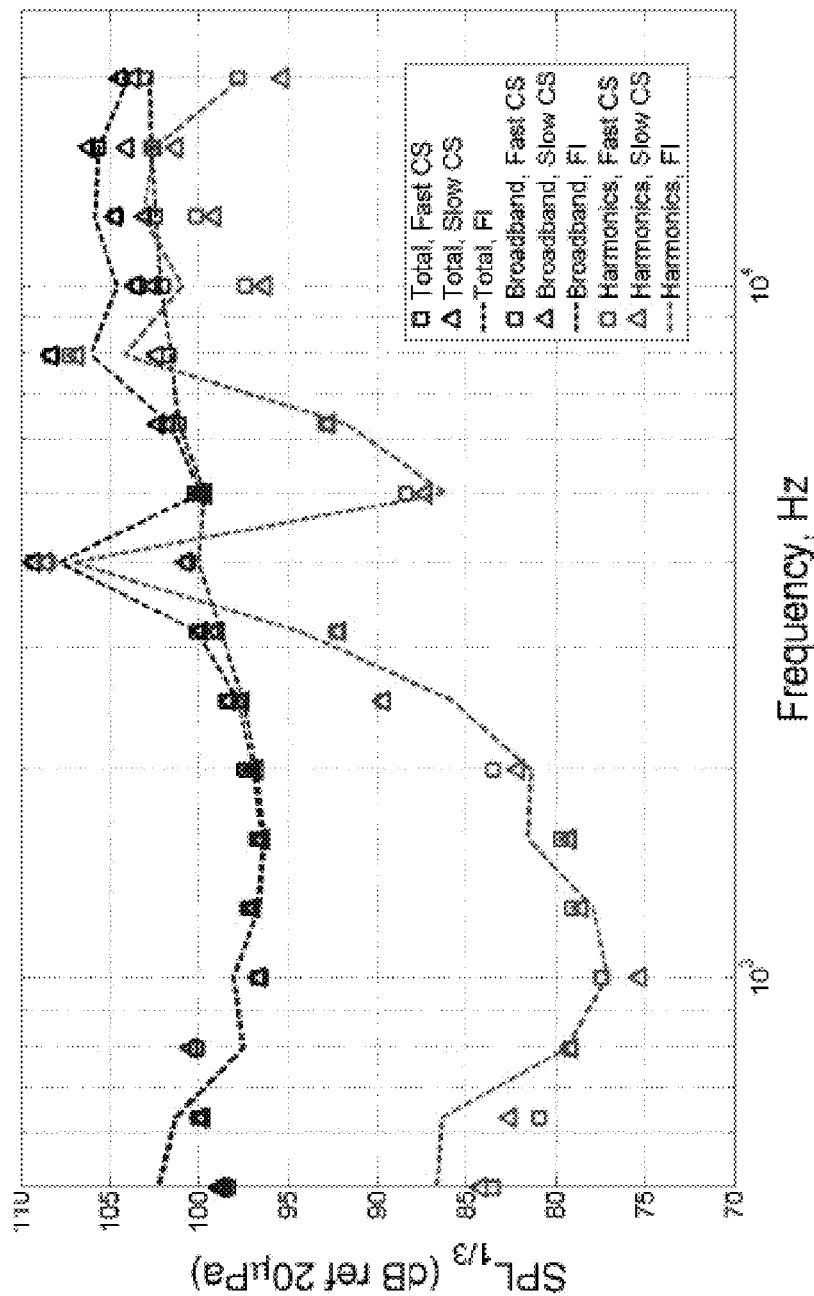

The time-domain Wold decomposition, as described above, separates shaft harmonics from the total signal, leaving only broadband content. In accordance with one example, for each run, three data subsets (broadband, harmonic, and total) were analyzed using the third-octave filtering and weighted averaging techniques associated with broadband spectral estimation. Because the one-third-octave filter settling time constants are relatively short, it is very effective to average the filtered data on the fly to describe the broadband directivities. Referring to FIG. 38 to FIG. 40, the three different center frequencies of 1000, 3981, and 15,849 Hz are selected to demonstrate that the Wold decomposition enables the continuous scan measurement technique to achieve very good reconstruction of the underlying directivity of both harmonic and broadband acoustic signal for regions of the sound field that are dominated by broadband, harmonics, or both. In fact, only small differences are seen several tens of decibels below the primary signal. The first frequency band (1000 Hz) contains negligible shaft harmonic content but does contain an aft dominant broadband noise signature, which may be partly attributable to jet noise from the model exhaust. The second (3981 Hz) and third (15,849 Hz) contain the first and fourth blade passing frequency (BPF) tones and their neighboring multiple pure tones (MPTs), respectively. Using interpolation at the locations $z=-1.02$ m ($q=114.5°$) and $z=+1.38$ m ($q=58.5°$), it may be seen in FIGS. 41 and 42 that there is good agreement between all three decomposed subsets (broadband, harmonic, total) between fixed-indexing and slow continuous-scan and fast continuous-scan cases.

Acoustic Holography Projection

Figure 43:
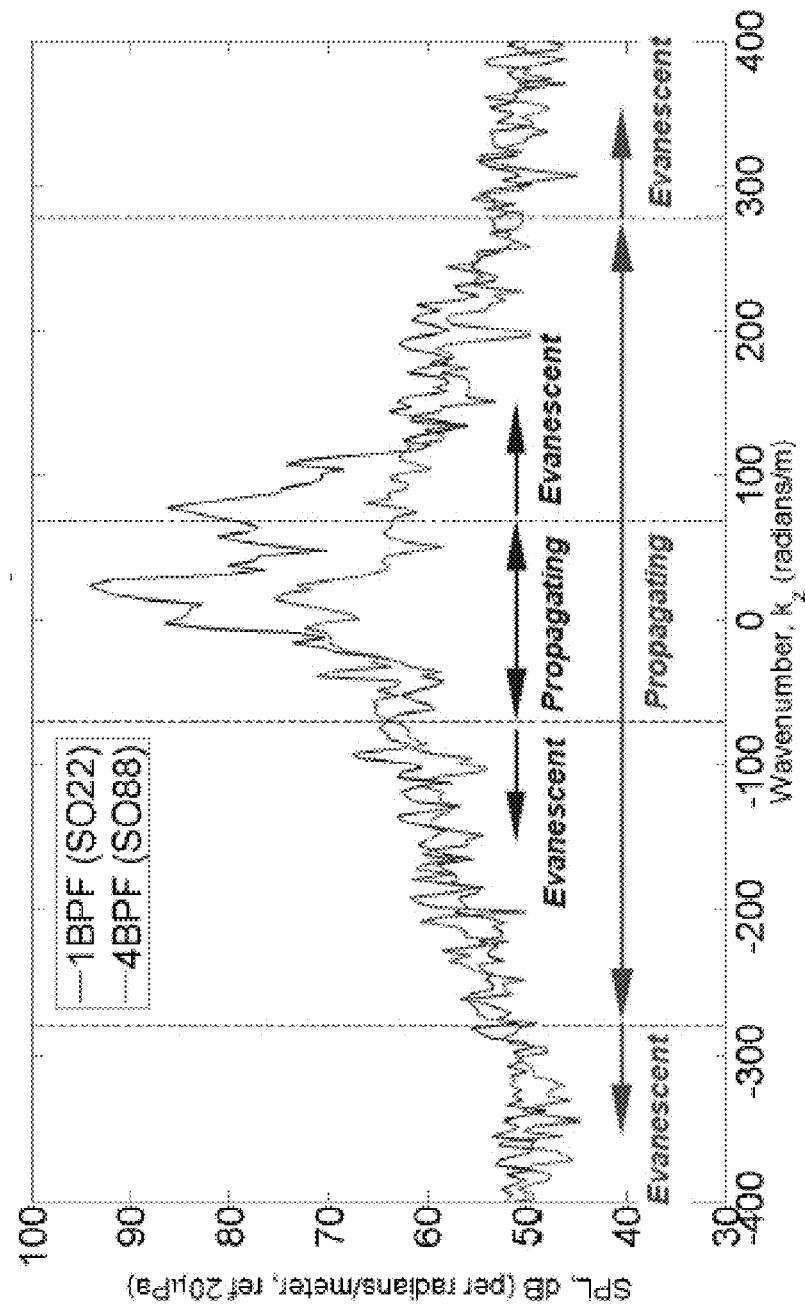
FIG. 43 is a graph depicting wavenumber spectra in accordance with various examples.

Acoustical holography (AH) projection of the measured data is based on the assumption that the partial fields have sufficient spatial resolution to describe the sound field in wavenumber space. In the absence of any azimuthal array coverage (i.e., since the data are acquired on a single scan line parallel to the model centerline), the azimuthal wavenumber, n, is assumed to be equal to the shaft order harmonic with sign given by the rotational direction of the fan. For a given partial field, the wavenumber spectrum may be plotted as shown in FIG. 43 for the 1 BPF and 4 BPF tones of the turbofan engine example. For each of these fields, the corresponding vertical dashed lines demarcate the boundary between propagating and evanescent wavenumbers, i.e., the boundaries of the so-called radiation circle. In general when there is significant evanescent energy present, as seen for the 1 BPF tone, the projection of data toward the source becomes more challenging because the signal must be exponentially inflated. In contrast, the evanescent content of the 4 BPF tone is well below the peak value, perhaps enabling an easier physical interpretation of the AH projection of primarily propagating wavenumbers both toward and away from the source.

Figure 44:
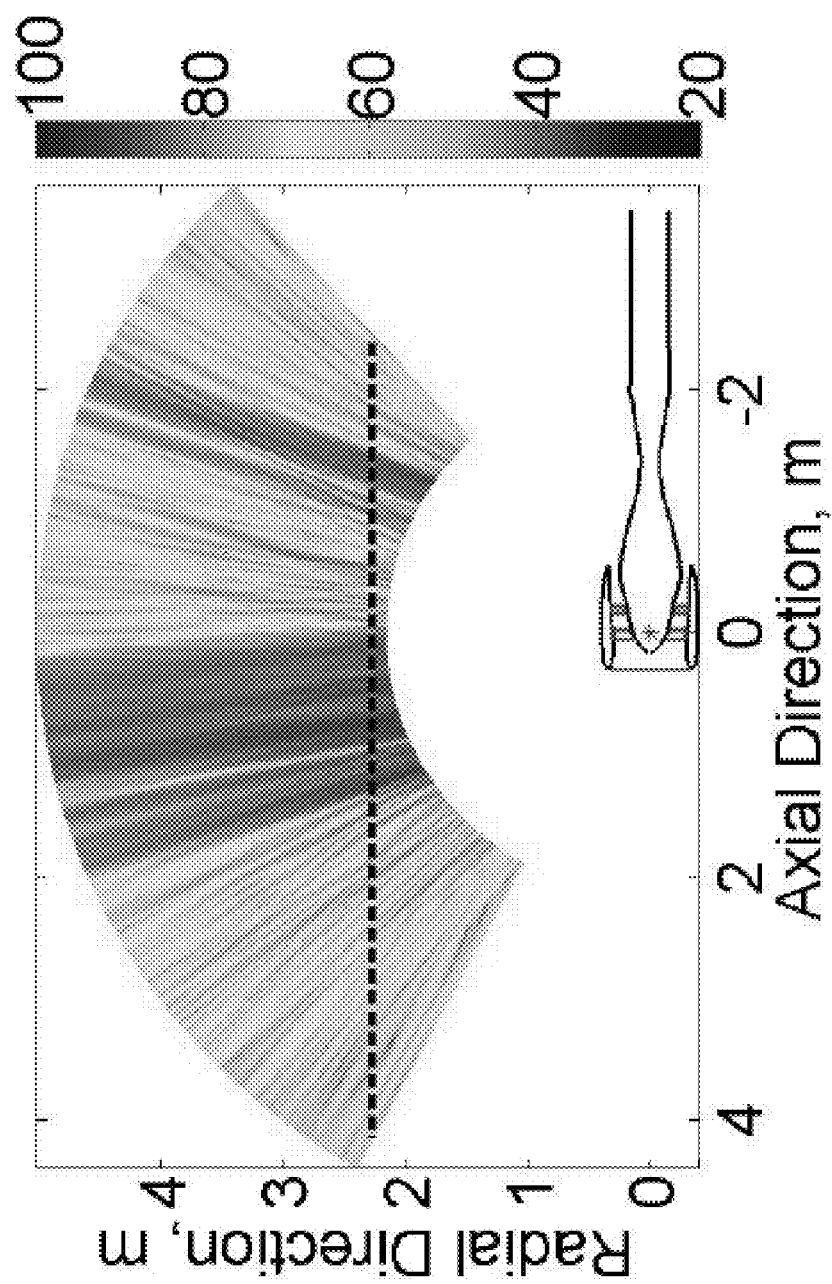
FIG. 44 is a graph depicting acoustic holography soundfield reconstructions in accordance with various examples.
Figure 45:
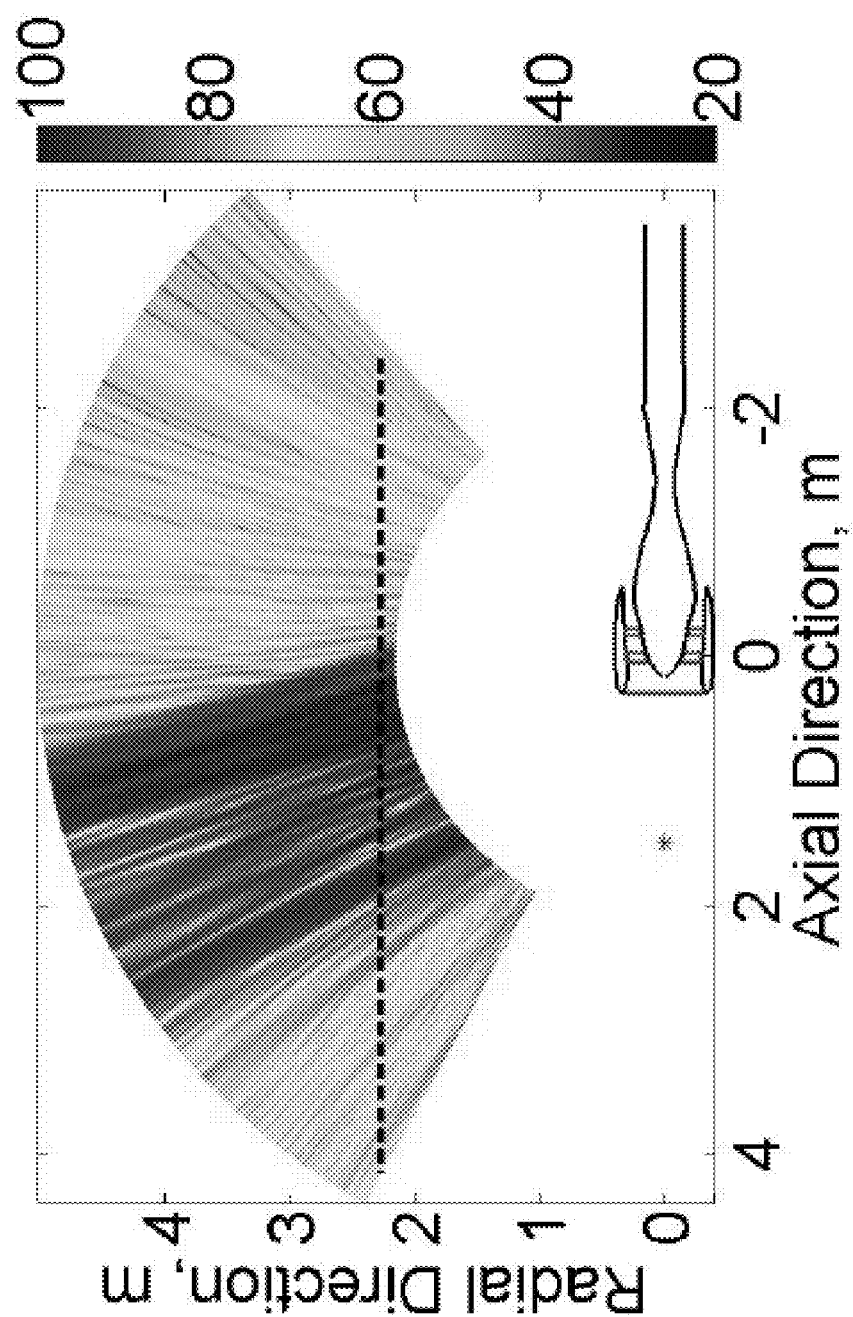
FIG. 45 is a graph depicting acoustic holography reconstructions in accordance with various examples.

FIG. 44 and FIG. 45 present acoustical holography reconstructions of the near-field region around the model turbofan under two different assumed source origins: longitudinal distance $z=0$ and $1.5$ m.

The partial field data is the input that comes from the scan line shown in dashed black. What is apparent is that the placement of the origin of the assumed source coordinate system affects the output directivity of the reconstructed sound field.

Figure 46:
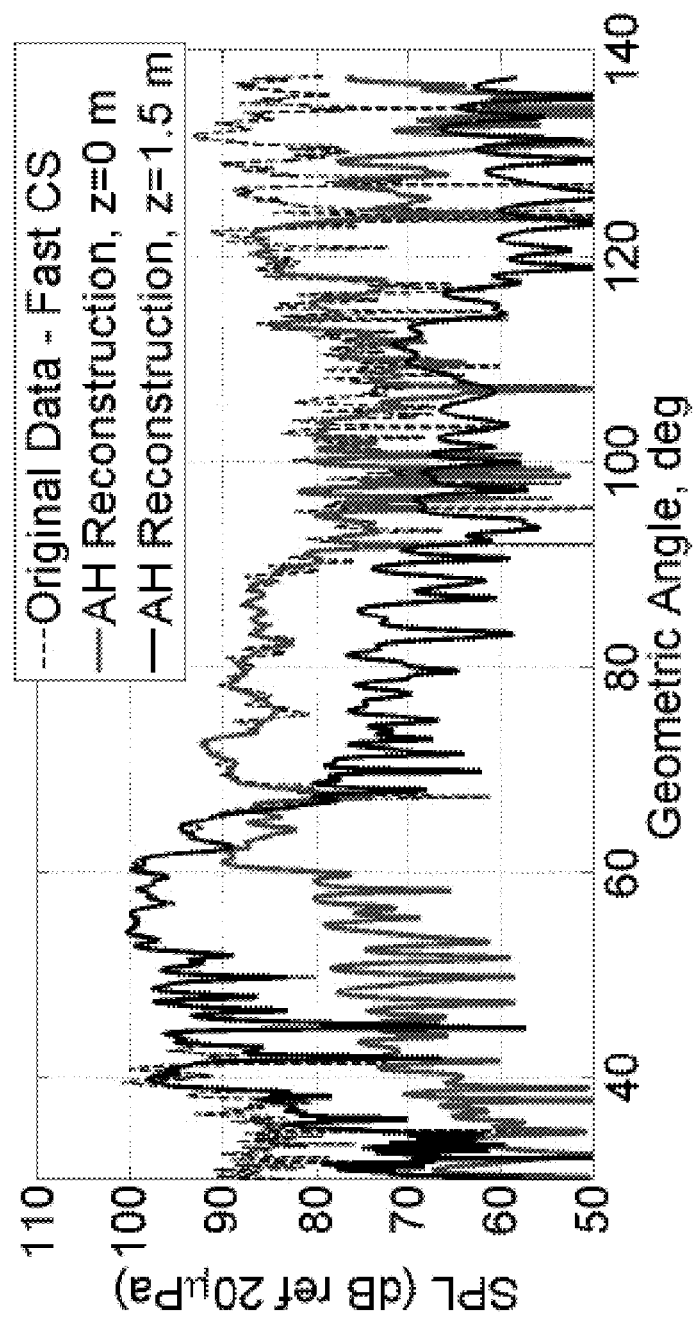
FIG. 46 is a graph depicting a complex envelope of an exemplary tone as a function of angle.

Specifically, when the origin is at $z=0$ m, the sound field tends to generally radiate in a broadside direction, whereas placement of the apparent source origin at $z=1.5$ m (upstream of the fan face) results in a directivity lobe pointed in a shallower direction from the inlet. The apparent relationship between the assumed source origin and the sound field directivity may be better understood by comparing the original complex envelope of the BPF 4 tone as a function of angle to the two reconstructions as shown in FIG. 46. Clearly, each simulation does a good job reconstructing the measured sound field along a limited sector of the measurement line that is near the sound source but falls short away from these locations. This suggests, perhaps, that a "patch" holography approach built on an assumption of a distribution of apparent sources may provide a means to reconstruct the total sound field. It should be noted that the reconstruction of a very complex, analytically generated multipole field emanating from an assumed origin has been verified to be accurate, and that the presence of nuisance sources located away from this origin may contaminate the total reconstruction.

While the use of AH techniques is relatively new for sources in a mean flow, one may speculate that such projection toward the source, when the wavenumber content allows it, provides insight into the origin of the noise and may also be a powerful diagnostic for locating spurious noise sources in a test facility. The present embodiments provide just a few possibilities of data analyses with the continuous-scan and holography paradigm. In further embodiment, AH methods may be applied to time-domain data generated by various numerical aeroacoustics simulations to gain an improved understanding of the capabilities and artifacts associated with this technology.

SUMMARY

It has been shown and described herein that the separation of shaft-order harmonic and broadband content in the time domain using the Vold-Kalman filter with a tachometer signal enables accurate and efficient measurement of the complex envelopes of harmonic sound fields from turbofan engines and other test subjects having rotating elements. Phase preservation of the harmonic content allows for advanced diagnostics of sources that are generally spatially correlated using acoustical holography to interpret the sound field. Furthermore, a significant improvement in resolution and a time reduction by an order of magnitude are potentially made feasible by switching from a fixed indexing acquisition to continuous acquisitions over a range of scan speeds.

While at least one example embodiment has been presented in the foregoing detailed description, it should be appreciated that a vast number of variations exist. It should also be appreciated that the example embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined herein, which includes known equivalents and foreseeable equivalents at the time of filing this patent application.

The invention claimed is:

1. A method of imaging a test subject, comprising:
providing one or more moveable sensors to sense an attribute of the test subject, the attribute having a tonal noise component and a broadband noise component;
providing a rotational sensor to sense a rotational velocity of a rotational element of the test subject;
moving each of the moveable sensors along a path while continuously acquiring: rotational sensor test data from the rotational sensor, the rotational sensor test data indicative of the rotational velocity of the rotational element; moveable sensor test data from the moveable sensors, the moveable sensor test data indicative of the sensed attribute; a position of each of the moveable sensors; and an orientation of each of the moveable sensors;
constructing a set of transfer functions corresponding to points in space that have been visited by the moveable sensors, each of the transfer functions relating the moveable sensor test data to the rotational sensor test data; and
producing a visual representation of the tonal noise component of the attribute in a region adjacent the test subject using the set of transfer functions.

2. The method of claim 1, further including:
providing one or more reference sensors to sense the attribute of the test subject; and
acquiring test data from the reference sensors while moving each of the moveable sensors along the path;
constructing the set of transfer functions based further on the test data of the reference sensors; and
producing a visual representation of the broadband noise component of the attribute in a region adjacent the test subject using the set of transfer functions.

3. The method of claim 1, wherein constructing the set of transfer functions includes applying a Vold-Kalman Order Filter to extract time histories of tones that are coherent with the rotational sensor.

4. The method of claim 1, further including applying Doppler correction to the rotational sensor to account for a relative velocity between the moveable sensors and the test subject.

5. The method of claim 1, wherein constructing the set of transfer functions further includes using Chebyshev-spaced trajectory points to achieve averaging between the points in space between the moveable sensors.

6. The method of claim 1, further including using a canonical coherence method to construct the set of transfer functions.

7. The method of claim 1, wherein the attribute is an acoustic attribute.

8. The method of claim 1, wherein the moveable sensors are fixed to a structure and are distributed linearly along a structure axis at substantially equal intervals along the structure.

9. The method of claim 8, wherein continuously moving the moveable sensors along the path includes rotating the structure around the test subject.

10. The method of claim 9, wherein the orientation of each moveable sensor with respect to the structure is substantially the same and generally faces the test subject.

11. A system for scanning a test subject, comprising:
one or more moveable sensors to continuously sense an attribute of the test subject during a test mode in which the one or more moveable sensors moves along a path with respect to the test subject, wherein the attribute has a tonal noise component and a broadband noise component;
a rotational sensor to sense a rotational velocity of a rotational element of the test subject;
a data acquisition system coupled to the moveable sensors and the rotational sensor, wherein during the test mode the data acquisition system acquires: moveable sensor test data from the moveable sensors, the moveable sensor test data associated with the sensed attribute; a position of each of the moveable sensors; an orientation of each of the moveable sensors; and rotational sensor test data from the rotational sensor, the rotational sensor test data indicative of the rotational velocity of the rotational element;
a processor to analyze the acquired data and construct a set of transfer functions relating the moveable sensor test data to the rotational sensor test data; and
a display for providing a visual representation of the tonal noise component of the attribute in a region adjacent the test subject using the set of transfer functions.

12. The system of claim 11, further including:
one or more reference sensors to sense the attribute of the test subject;
wherein the data acquisition system is further configured to acquire test data from the reference sensors while moving each of the moveable sensors along the path;
wherein the processor is further configured to construct the set of transfer functions based in part on the test data of the reference sensors; and
wherein the display further provides a visual representation of the broadband noise component of the attribute in a region adjacent the test subject using the set of transfer functions.

13. The system of claim 11, wherein constructing the set of transfer functions includes applying a Vold-Kalman Order Filter to extract time histories of tones that are coherent with the rotational sensor.

14. The system of claim 11, wherein the processor is further configured to apply Doppler correction to the rotational sensor to account for a relative velocity between the moveable sensors and the test subject.

15. The system of claim 11, wherein the attribute is an acoustic attribute.

16. The system of claim 11, wherein the moveable sensors are fixed to a structure and are distributed linearly along a structure axis at substantially equal intervals along the structure.

17. The system of claim 16, wherein the path includes rotating the structure around the test subject.

18. The system of claim 17, wherein the orientation of each moveable sensor with respect to the structure is substantially the same and generally faces the test subject.

19. A method of imaging a test subject, comprising:
moving a plurality of moveable sensors along a path around the test subject while continuously acquiring acoustic test data that is indicative of an acoustic property of the test subject and rotational test data associated with a rotational velocity of an element of the test subject;
constructing a set of transfer functions corresponding to points in space that have been visited by the plurality of moveable sensors, each of the transfer functions relating the acoustic test data acquired by the plurality of moveable sensors to the rotational test data associated with the rotational velocity; and producing a visual representation of a tonal noise component of the acoustic property in a region adjacent the test subject using the set of transfer functions.

20. The method of claim 19, further including:

acquiring test data from a set of reference sensors while moving the plurality of moveable sensors along the path;

constructing the set of transfer functions based further on the test data of the reference sensors; and producing a visual representation of a broadband noise component of the attribute in a region adjacent the test subject using the set of transfer functions.

\* \* \* \* \*